US009119668B2

(12) United States Patent
Marka et al.

(10) Patent No.: US 9,119,668 B2
(45) Date of Patent: Sep. 1, 2015

(54) SURGICAL LAMPS AND METHODS FOR ILLUMINATING OPERATING SITES

(71) Applicant: TRUMPF Medizin Systeme GmbH + Co. KG, Saalfeld (DE)

(72) Inventors: Rudolf Marka, Ismaning (DE); Rouven Rosenheimer, Munich (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 132 days.

(21) Appl. No.: 14/014,740

(22) Filed: Aug. 30, 2013

(65) Prior Publication Data

US 2014/0066722 A1 Mar. 6, 2014

Related U.S. Application Data

(63) Continuation of application No. PCT/EP2012/053682, filed on Mar. 2, 2012.

(30) Foreign Application Priority Data

Mar. 2, 2011 (EP) .................................... 11156645

(51) Int. Cl.
*A61B 1/06* (2006.01)
*A61B 19/00* (2006.01)
(Continued)

(52) U.S. Cl.
CPC ............... *A61B 19/5202* (2013.01); *A61B 1/06* (2013.01); *A61B 17/52* (2013.01); *A61B 19/52* (2013.01); *F21V 14/02* (2013.01); *F21V 23/0442* (2013.01); *A61B 2017/00057* (2013.01);
(Continued)

(58) Field of Classification Search
CPC ........... A61B 1/06; A61B 2017/00057; A61B 19/52; A61B 19/5202; F21V 14/02; F21V 23/0442
USPC ....................... 362/249.02, 800, 804; 600/249
See application file for complete search history.

(56) References Cited

U.S. PATENT DOCUMENTS 4,884,008 A 11/1989 Bossler
5,038,261 A 8/1991 Kloos
(Continued)

FOREIGN PATENT DOCUMENTS

CN 101446403 A 6/2009
EP 0299196 A2 1/1989
(Continued)

OTHER PUBLICATIONS

DIN EN 60601-2-41 (VDE 0750-2-41): May 2010, 50 pages, with English translation of excerpts, May 2010.*

(Continued)

*Primary Examiner* — Larry E Waggle, Jr.
(74) *Attorney, Agent, or Firm* — Fish & Richardson P.C.

(57) ABSTRACT

A surgical lamp for illuminating an operating site includes a lamp body that includes first and second light sources that respectively generate first and second light fields of different diameter on the operating site. When a change in a distance between the lamp body and the operating site is detected, the first and second light intensities of the first and second light sources, respectively, can be controlled such that the predetermined diameter (dx) at which the preset relative central illuminance (Ecx) of the resultant light field is generated is maintained at a substantially constant value as the distance changes.

40 Claims, 17 Drawing Sheets

(51) Int. Cl.
- *A61B 17/52* (2006.01)
- *F21V 14/02* (2006.01)
- *F21V 23/04* (2006.01)
- *A61B 17/00* (2006.01)
- *F21S 2/00* (2006.01)
- *F21S 8/06* (2006.01)
- *F21V 5/04* (2006.01)
- *F21V 21/30* (2006.01)
- *F21V 21/40* (2006.01)
- *F21W 131/205* (2006.01)
- *F21Y 101/02* (2006.01)
- *F21Y 105/00* (2006.01)
- *F21Y 113/00* (2006.01)

(52) U.S. Cl.
CPC . *A61B2017/00106* (2013.01); *A61B 2019/461* (2013.01); *F21S 2/005* (2013.01); *F21S 8/06* (2013.01); *F21V 5/048* (2013.01); *F21V 21/30* (2013.01); *F21V 21/403* (2013.01); *F21W 2131/205* (2013.01); *F21Y 2101/02* (2013.01); *F21Y 2105/001* (2013.01); *F21Y 2113/005* (2013.01)

(56) References Cited

U.S. PATENT DOCUMENTS

| | | | |
|---|---|---|---|
| 5,068,767 A | 11/1991 | Koyama | |
| 7,483,220 B2 * | 1/2009 | Kittelmann et al. | 359/742 |
| 2009/0318772 A1 * | 12/2009 | Marka et al. | 600/249 |
| 2011/0037840 A1 | 2/2011 | Hiltl | |

FOREIGN PATENT DOCUMENTS

| | | |
|---|---|---|
| EP | 0422331 A2 | 4/1991 |
| EP | 2136128 A1 | 12/2009 |
| EP | 2215987 A1 | 8/2010 |
| EP | 2283790 A1 | 2/2011 |

OTHER PUBLICATIONS

Notification of Transmittal of Translation of the International Preliminary Report on Patentability and Written Opinion from corresponding PCT Application No. PCT/EP2012/053682, mailed Sep. 12, 2013, 15 pages.

DIN EN 60601-2-41 (VDE 0750-2-41):May 2010, 50 pages, with English translation of excerpts, May 2010.

* cited by examiner

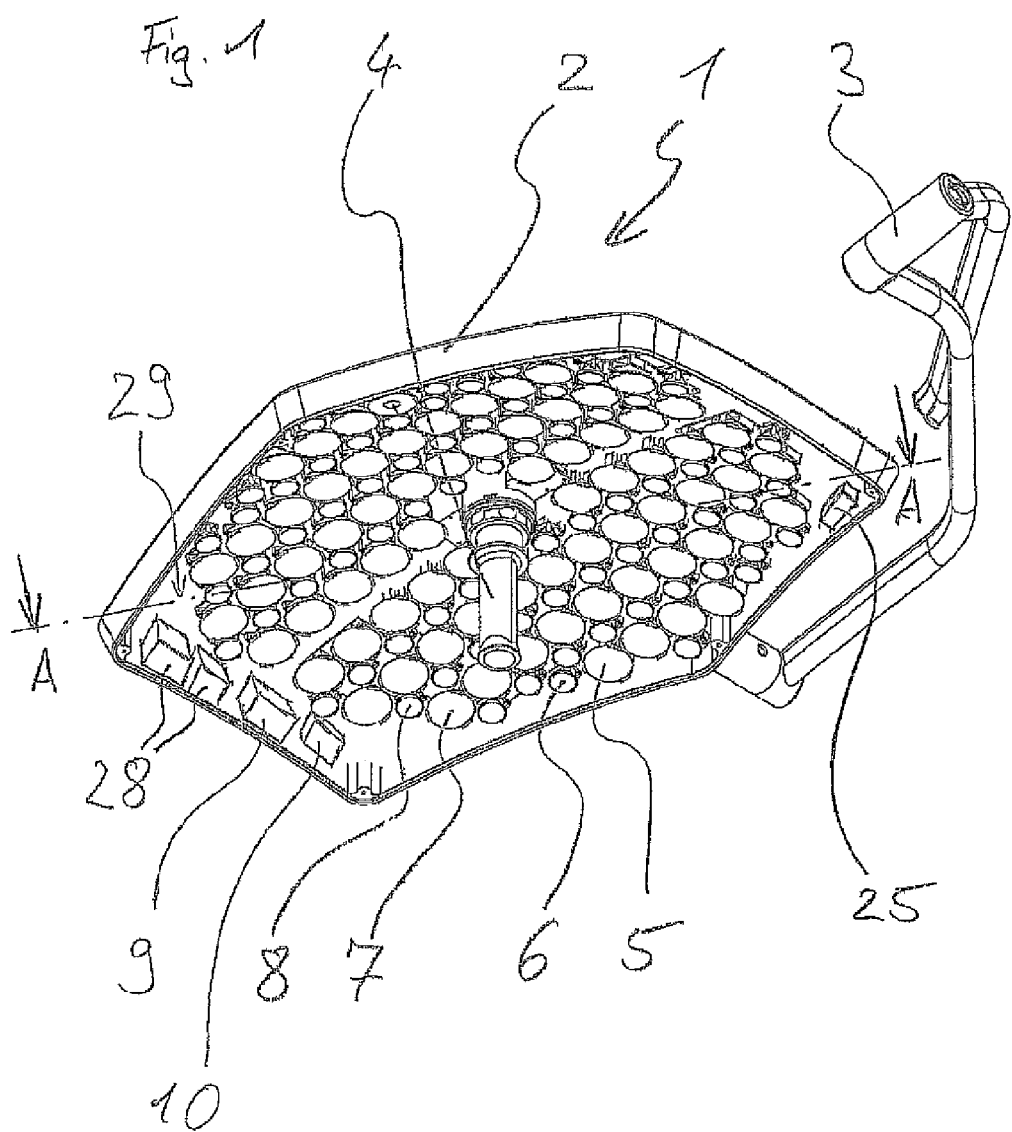

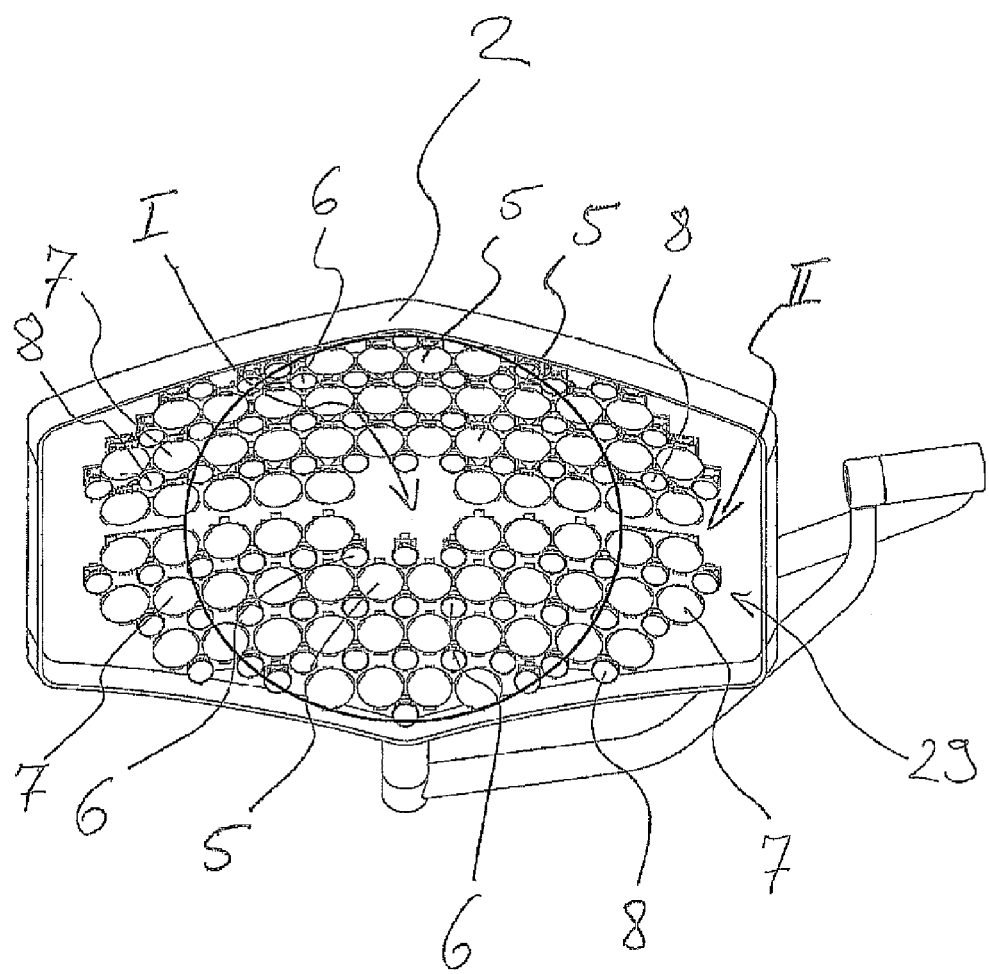

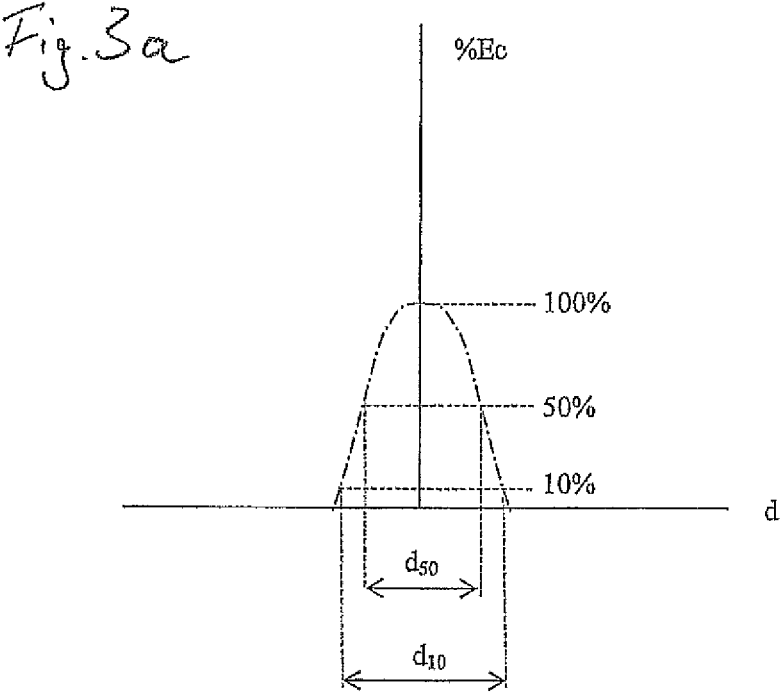

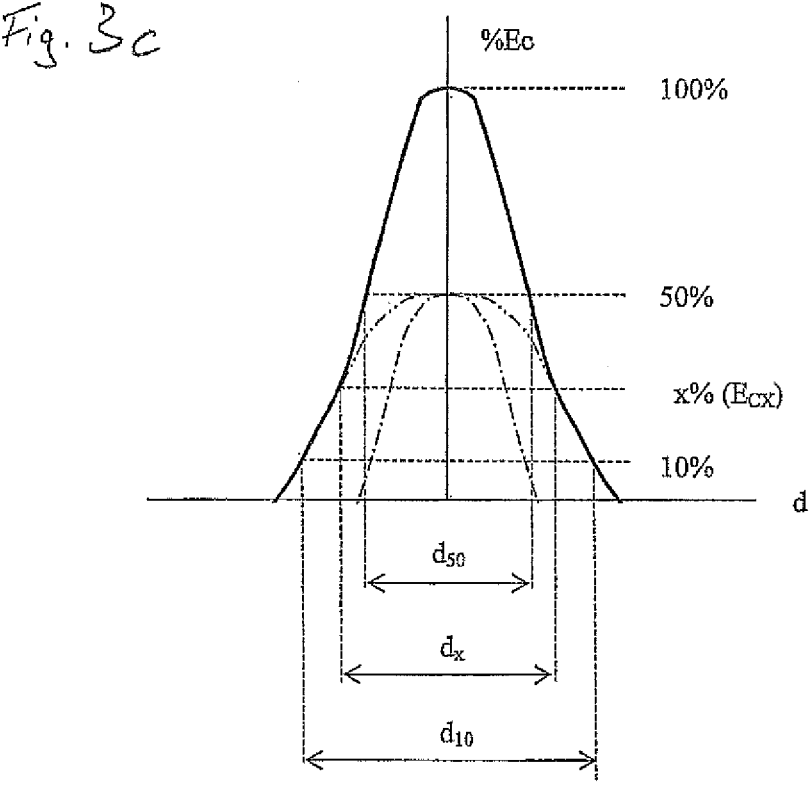

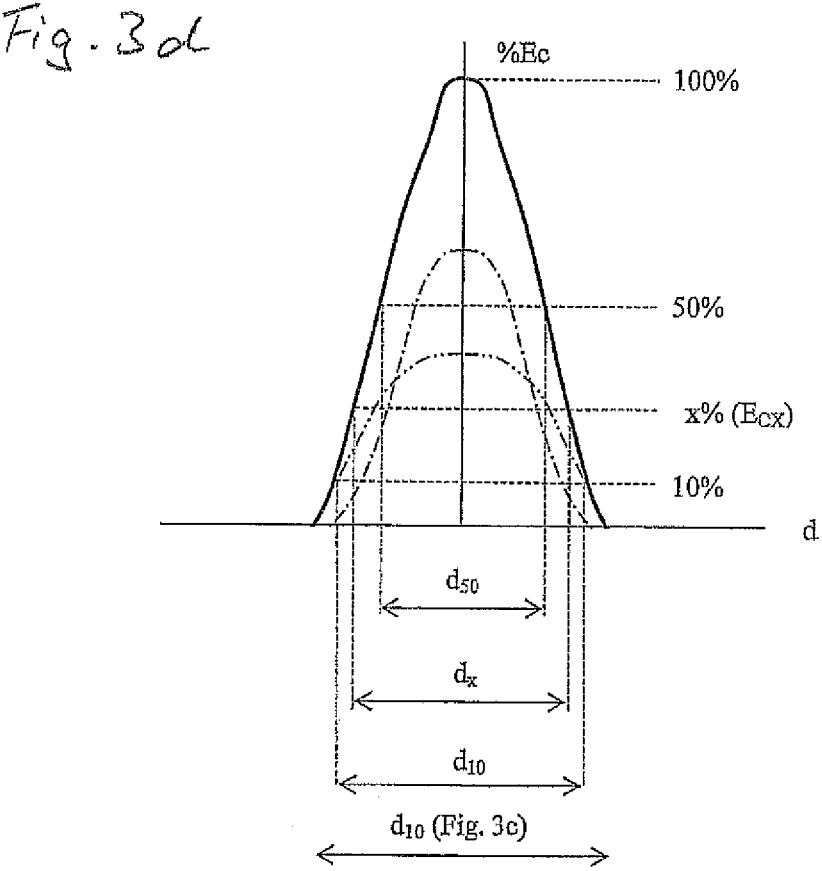

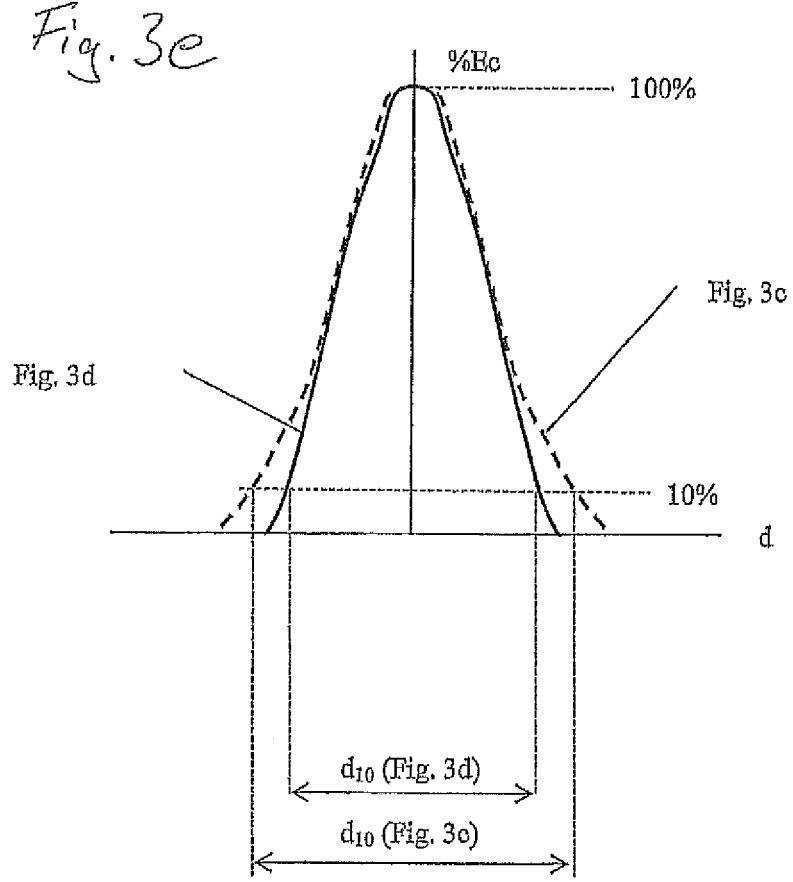

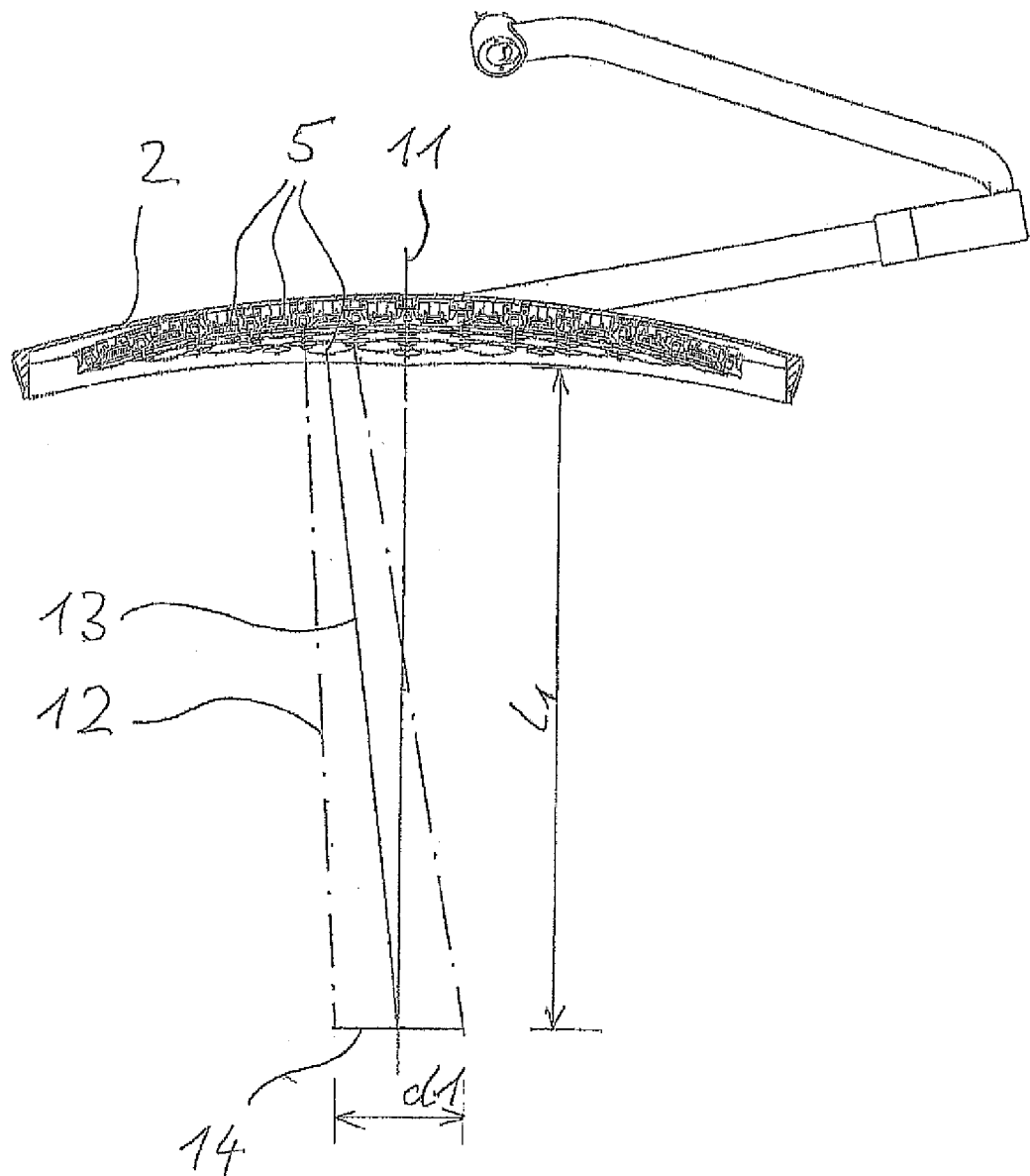

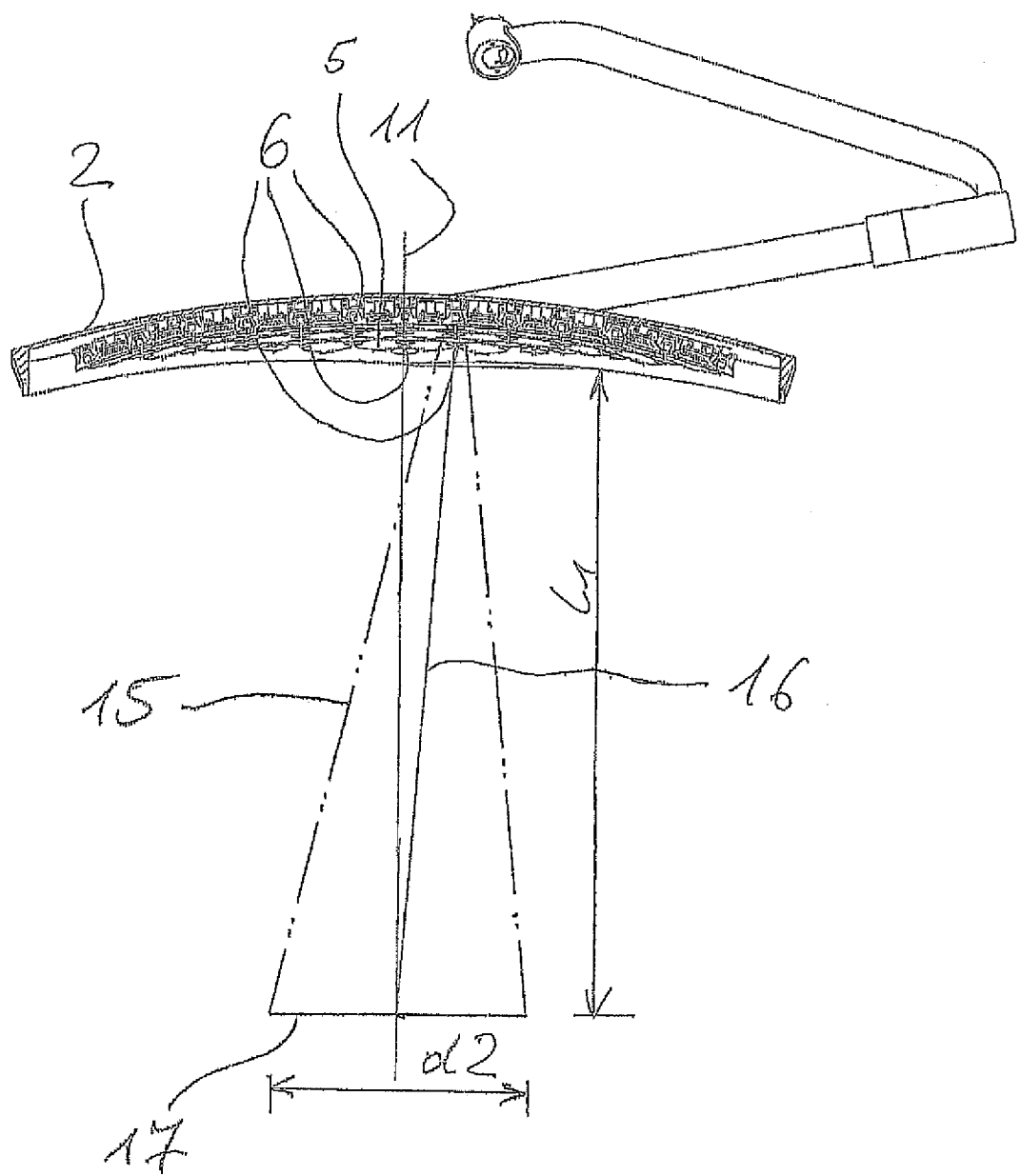

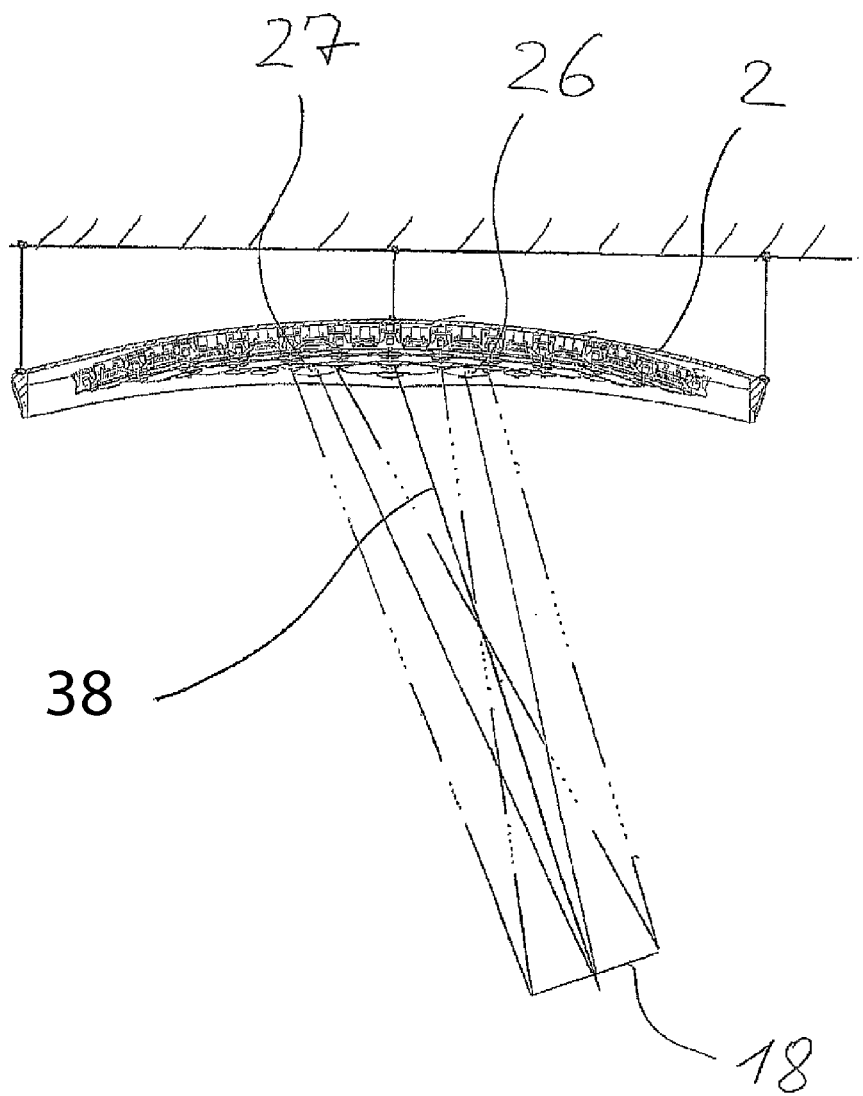

SURGICAL LAMPS AND METHODS FOR ILLUMINATING OPERATING SITES

CROSS REFERENCE TO RELATED APPLICATIONS

This application is a continuation of and claims priority under 35 U.S.C. §120 to PCT Application No. PCT/EP2012/053682 filed on Mar. 2, 2012, which claimed priority to European Application No. 11 156 645.1, filed on Mar. 2, 2011. The contents of both of these priority applications are hereby incorporated by reference in their entirety.

TECHNICAL FIELD

The present disclosure relates to surgical lamps, such as surgical lamps that generate light fields whose light field diameters do not change as a working distance of the surgical lamps changes.

BACKGROUND

Surgeons can adjust various parameters of a surgical lamp to achieve good illumination of an operating site during surgical procedures. Such parameters may include a position and/or an orientation of a lamp body of the surgical lamp, a focus of light beams radiated from the surgical lamp, and an intensity of light radiated from the surgical lamp (e.g., an illuminance on the operating site). The position and/or the orientation of the lamp body is typically adjusted (thereby causing an adjustment of a light field generated by the lamp body) by the surgeon. The surgeon may effect such changes by manipulating a sterile handle attached to the lamp body to move (e.g., swivel) the lamp body to a desired position and/or desired orientation. In some cases, repositioning the handle may cause a change in an intersection point of the light beams radiated from the lamp body.

Some surgical lamps may include mechanisms for measuring a distance between the lamp body and the operating site and accordingly correct the intensity of the radiated light in order to maintain a constant central illuminance on the operating site. In such surgical lamps, while the central illuminance is adjusted, the light field diameter does not change because light sources of the surgical lamp are non-adjustable, and parallel spotlights that may otherwise address this problem are not implemented in such optical setups.

SUMMARY

A surgical lamp is configured such that a light field diameter of a light field generated by the surgical lamp remains constant as the working distance of the surgical lamp changes.

In one aspect of the invention, a surgical lamp for illuminating an operating site includes a lamp body having an optical axis and including a first light source and a second light that respectively generate a first light field and a second light field on the operating site. The operating site is located at a particular distance from the lamp body, and the first and second light fields together produce a resultant light field, wherein the resultant light field has a circular shape and is associated with a light distribution that conforms with a surgical lamp standard, such that a preset relative central illuminance (Ecx) of the light distribution is generated at a predetermined diameter (dx) of the resultant light field. The surgical lamp further includes a control device configured to control a first light intensity of the first light source and a second light intensity of the second light source, such that the preset relative central illuminance (Ecx) is generated at the predetermined diameter (dx) at the particular distance. The surgical lamp further includes a device for detecting a distance between the lamp body and the operating site, wherein the control device is configured to control the first and second light intensities of the first and second light sources, respectively, such that the predetermined diameter (dx) of the resultant light field on the operating site is maintained at a substantially constant value as the distance between the lamp body and the operating site changes.

In another aspect of the invention, a method for operating a surgical lamp includes detecting a change in a distance between a lamp body of the surgical lamp and an operating site, wherein the lamp body has an optical axis and includes a first light source and a second light that respectively generate a first light field and a second light field on the operating site. The operating site is located at a particular distance from the lamp body, and the first and second light fields together produce a resultant light field, wherein the resultant light field has a circular shape and is associated with a light distribution that conforms with a surgical lamp standard, such that a preset relative central illuminance (Ecx) of the light distribution is generated at a predetermined diameter (dx) of the resultant light field. The surgical lamp further includes a control device configured to control a first light intensity of the first light source and a second light intensity of the second light source, such that the preset relative central illuminance (Ecx) is generated at the predetermined diameter (dx) at the particular distance. The surgical lamp further includes a device for detecting the distance between the lamp body and the operating site, wherein the control device is configured to control the first and second light intensities of the first and second light sources, respectively, such that the predetermined diameter (dx) of the resultant light field on the operating site is maintained at a constant value when the distance between the lamp body and the operating site changes. The method further includes controlling the first and second light intensities of the first and second light sources, respectively, such that the predetermined diameter (dx) at which the preset relative central illuminance (Ecx) is generated is maintained at a substantially constant value as the distance between the lamp body and the operating site changes.

In another aspect of the invention, a surgical lamp for illuminating an operating site located along an optical axis includes a lamp body from which the optical axis extends, including a first light source and a second light source that respectively generate a first light field and a second light field having diameters that are substantially equal, wherein the operating site is located at a particular distance from the lamp body along the optical axis. The first light field is associated with a first light distribution and the second light field is associated with a second light distribution that is substantially equal to the first light distribution. The first light source has a fixed orientation with respect to a light-emitting surface of the lamp body, and the second light source has an adjustable orientation with respect to the light-emitting surface of the lamp body. The first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the optical axis. The surgical lamp further includes a control device configured to control a first light intensity of the first light source, a second light intensity of the second light source, and a tilting angle of the second light source, such that the preset relative central illuminance (Ecx) is generated at the predetermined diameter (dx) at the particular distance. The surgical lamp further includes a device for detecting a distance between the lamp body and the operating site along the optical axis, wherein the control device is configured to control the first and second light intensities of the first and second light sources, respectively, and the tilting angle of the second light source, such that the predetermined diameter (dx) of the resultant light field is maintained at a substantially constant value as the distance along the optical axis between the lamp body and the operating site changes.

In another aspect of the invention, a method for operating a surgical lamp includes detecting a change in a distance along an optical axis of the surgical lamp between a lamp body of the surgical lamp and an operating site, wherein the optical axis extends from the lamp body, and the lamp body includes a first light source and a second light source that respectively generate a first light field and a second light field having diameters that are equal. The operating site is located at a particular distance from the lamp body along the optical axis. The first light field is associated with a first light distribution and the second light field is associated with a second light distribution that is equal to the first light distribution. The first light source has a fixed orientation with respect to a light-emitting surface of the lamp body, and the second light source has an adjustable orientation with respect to the light-emitting surface of the lamp body. The first and second light fields together produce a resultant light field that has a circular shape and is associated with a resultant light distribution that conforms to a surgical lamp standard, such that a preset relative central illuminance (Ecx) of the light distribution is generated at a predetermined diameter (dx) of the resultant light field along the optical axis. The surgical lamp further includes a control device configured to control a first light intensity of the first light source, a second light intensity of the second light source, and a tilting angle of the second light source, such that the preset relative central illuminance (Ecx) is generated at the predetermined diameter (dx) at the particular distance. The surgical lamp further includes a device for detecting a distance between the lamp body and the operating site along the optical axis, wherein the control device is configured to control the first and second light intensities of the first and second light sources, respectively, and the tilting angle of the second light source such that the predetermined diameter (dx) of the resultant light field is maintained at a substantially constant value as the distance between the lamp body and the operating site changes. The method further includes controlling the first and second light intensities of the first and second light sources, respectively, and the tilting angle of the second light source, such that the predetermined diameter (dx) at which the preset relative central illuminance (Ecx) is generated is maintained at a constant value as the distance along the optical axis between the lamp body and the operating site changes.

In another aspect of the invention, a surgical lamp for illuminating an operating site located along a tiltable optical axis of the surgical lamp includes a lamp body from which the tiltable optical axis extends, including a first light source and a second light source that respectively generate a first light field and a second light field having diameters that are substantially equal. The operating site is located at a particular distance from the lamp body along the tiltable optical axis. The first light field is associated with a first light distribution and the second light field is associated with a second light distribution that is substantially equal to the first light distribution. The first and second light sources are tiltable with respect to a light-emitting surface of the lamp body. The first light source emits a light sheaf that defines the tiltable optical axis. The first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the tiltable optical axis. The surgical lamp further includes a control device configured to control a first light intensity of the first light source, a second light intensity of the second light source, and first and second tilting angles of the first and second light sources, respectively, such that the preset relative central illuminance (Ecx) is generated at the predetermined diameter (dx) at the particular distance. The surgical lamp further includes a device for detecting a distance between the lamp body and the operating site along the tiltable optical axis. The control device is configured to control the first and second light intensities and the first and second tilting angles of the first and second light sources, respectively, such that the predetermined diameter (dx) of the resultant light field is maintained at a substantially constant value as the distance along the tiltable optical axis between the lamp body and the operating site changes.

In some embodiments, the surgical lamp further includes a means for triggering adjustment of light intensities of light sources of the lamp body.

In certain embodiments, the control device is configured to ensure that a central illuminance (Ec) of the resultant light field conforms to the surgical lamp standard as the distance changes.

In some embodiments, at least one of the first and second light sources is tiltable with respect to a light-emitting surface of the lamp body.

In certain embodiments, the surgical lamp further includes modules to which at least one of the first and second light sources is attached, wherein the modules are tiltable with respect to each other.

In some embodiments, the lamp body includes a light-emitting surface that is divided into a an inner area (I) that has a circular shape and at least one outer area (II) positioned adjacent the inner area (I), wherein the first and second light sources are positioned along the inner area (I) and have first and second orientations, respectively, that are fixed with respect to the light-emitting surface. The lamp body further includes a third light source and a fourth light source that respectively generate a third light field and a fourth light field having different diameters, the third and fourth light fields together with the first and second light fields generating the resultant light field. The third and fourth light sources are positioned along the at least one outer area (II) and are tiltable with respect to the light-emitting surface of the lamp body. The lamp body further comprises a driving device for respectively tilting the third and fourth light sources to a third tilting angle and a fourth tilting angle. The control device is configured to control a third light intensity of the third light source, a fourth light intensity of the fourth light source, and the driving device, such that the predetermined diameter (dx) of the resultant light field on the operating site is maintained at a substantially constant value as the distance between the lamp body and the operating site changes.

In certain embodiments, the means for triggering adjustment of the light intensities includes a motion sensor, and the control device is configured to evaluate a detected distance between the lamp body and the operating site, such that the control device appropriately controls the first, second, third, and fourth light sources following detection of a completed motion of the lamp body by the motion sensor.

In some embodiments, the first light source includes a first lens and the second light source includes a second lens, and the first and second lenses have different optically effective surfaces configured to generate light fields that have different light distributions.

In certain embodiments, the first light source includes a first lens and the second light source includes a second lens, and the first and second lenses have different diameters.

In some embodiments, the surgical lamp further includes an input means connected to the control device for setting the predetermined diameter (dx) at which the preset relative illuminance (Ecx) of the resultant light field is generated.

In certain embodiments, the input means includes a means for selecting among different preset diameters (dx) at which the preset relative illuminance (Ecx) is generated.

In some embodiments, the surgical lamp standard is DIN EN 60601-2-41:2010.

In certain embodiments, light sources of the lamp body are assigned to groups according to one or more criteria including a diameter of a light field generated by the light sources and a distance of the light source from the optical axis, wherein the control device is configured such that the light sources within a group can be controlled similarly, and the groups of light sources can be controlled independently of one another.

In some embodiments, the control device includes a storage that stores a mapping, and the light intensities of the light sources in the groups are stored as force values associated with currents in the mapping, such that the force values are retrievable by the control device in a mixing ratio that depends on the distance between the lamp body and the operating site.

In certain embodiments, one or more of the light sources are tiltable with respect to a light-emitting surface of the lamp body, and tilting angles of the one or more light sources depend on the distance between the lamp body and the operating site, and the tilting angles are stored in the storage of the control device and are retrievable by the control device according to the distance between the lamp body and the operating site.

In some embodiments, the predetermined diameter (dx) is a factory preset value.

In certain embodiments, a central illuminance (Ec) of the resultant light field is factory preset value.

In some embodiments, an adjustment of the first and second light intensities to maintain the predetermined diameter (dx) at the constant value is triggered following a change in the distance between the lamp body and the operating site.

In certain embodiments, the first light field has a relatively small diameter and the second light field has a relatively large diameter, wherein preventing an increase in the predetermined diameter (dx) of the resultant light field includes increasing the first light intensity of the first light source and/or decreasing the second light intensity of the second light source, and wherein preventing a decrease in the predetermined diameter (dx) of the resultant light field includes decreasing the first light intensity of the first light source and/or increasing the second light intensity of the second light source.

In some embodiments, when the resultant light field is located at a maximum working distance, the predetermined diameter (dx) of the resultant light field is no greater than a minimum allowable predetermined diameter (dx).

In certain embodiments, when the resultant light field is located at a distance greater than a maximum working distance, the predetermined diameter (dx) of the resultant light field is no greater than a minimum allowable predetermined diameter (dx).

In some embodiments, the surgical lamp further includes a means for triggering adjustment of light intensities and/or tilting angles of light sources of the lamp body.

In certain embodiments, the control device is configured to ensure that a central illuminance (Ec) of the resultant light field conforms to the surgical lamp standard as the distance changes.

In some embodiments, the surgical lamp further includes modules to which at least one of the first and second light sources are attached, wherein the first light source is attached to an inner module of the modules, and the second light source is attached to another module of the modules.

In certain embodiments, a light-emitting surface of the lamp body or a light-emitting surface of the inner module is divided into an inner area (I) that has a substantially circular shape and at least one outer area (II) positioned adjacent the inner area (I), wherein the first light source is positioned along the inner area (I), and the second light source is positioned along the at least one outer area (II).

In some embodiments, the means for triggering an adjustment of the light intensities or the tilting angle includes a motion sensor, and the control device is configured to evaluate a detected distance between the lamp body and the operating site, such that the control device appropriately controls the first and second light sources following detection of a completed motion of the lamp body by the motion sensor.

In certain embodiments, the surgical lamp further includes an input means connected to the control device for setting the predetermined diameter (dx) at which the preset relative central illuminance (Ecx) of the resultant light field is generated.

In some embodiments, the input means includes a means for selecting among different preset diameters (dx) at which the preset relative central illuminance (Ecx) is generated.

In certain embodiments, light sources of the lamp body are assigned to groups according to a tilting capability of the light sources, wherein the control device is configured such that the light sources within a group can be controlled similarly, and groups of light sources can be controlled independently of one another.

In some embodiments, the control device includes a storage that stores a mapping, wherein tilting angles of the light sources are stored in the storage, and wherein the light intensities of the light sources in the groups are stored as force values associated with currents in the mapping, such that the tilting angles and the force values are retrievable by the control device in a mixing ratio that depends on the distance between the lamp body and the operating site.

In certain embodiments, the predetermined diameter (dx) is a factory preset value.

In some embodiments, a central illuminance (Ec) of the resultant light field is a factory preset value.

In certain embodiments, an adjustment of the first and second light intensities and/or an adjustment of the tilting angle to maintain the predetermined diameter (dx) at a constant value are triggered following a change in the distance between the lamp body and the operating site.

In some embodiments, preventing an increase in the predetermined diameter (dx) of the resultant light field includes tilting the second light source radially towards the optical axis and controlling the first and second light intensities of the first and second light sources, respectively, such that the predetermined diameter (dx) at which the relative central illuminance (Ecx) is generated is maintained at a substantially constant value, and preventing a decrease in the predetermined diameter (dx) of the resultant light field includes tilting the second light source radially away from the optical axis and controlling the first and second light intensities of the first and second light sources, respectively, such that the predetermined diameter (dx) at which the relative central illuminance (Ecx) is generated is maintained at a substantially constant value.

In certain embodiments, the control device is configured to ensure that a central illuminance (Ec) of the resultant light field conforms to the surgical lamp standard as the distance along the optical axis changes, preventing an increase in the predetermined diameter (dx) further includes controlling the first and second light intensities of the first and second light sources, respectively, such that the central illuminance (Ec) of the resultant light field is maintained at a substantially constant value, and preventing an increase in the predetermined diameter (dx) further includes controlling the first and second light intensities of the first and second light sources, respectively, such that the central illuminance (Ec) of the resultant light field is maintained at a substantially constant value.

In some embodiments, when the resultant light field is located at a maximum allowable distance or at a distance greater than the maximum allowable distance, the predetermined diameter (dx) of the resultant light field is no greater than a minimum allowable predetermined diameter (dx).

In some embodiments, the light field generated by a tiltable light source is shifted by controlling a tilting angle of the tiltable light source such that the predetermined diameter at which a preset relative central illuminance of the resultant light field is generated is maintained at a constant value as the distance between the lamp body and the operating site changes.

Other aspects, features, and advantages will be apparent from the description, the drawings, and the claims.

DESCRIPTION OF DRAWINGS

FIG. 1 shows a perspective view of a surgical lamp.

FIG. 2 shows a perspective view of a lamp body of the surgical lamp of FIG. 1.

FIG. 3a shows a graph of a light distribution generated by a first light source of the surgical lamp of FIG. 1.

FIG. 3b shows a graph of a light distribution generated by a second light source of the surgical lamp of FIG. 1.

FIG. 3c shows a graph of a light distribution resulting from a superposition of the light distributions of FIGS. 3a and 3b.

FIG. 3d shows a graph of a light distribution resulting from a superposition of two light distributions different from those of FIGS. 3a and 3b.

FIG. 3e shows a graph of the light distributions of FIGS. 3c and 3d.

FIG. 4a shows a cross-sectional view of the lamp body of FIG. 2 and a light field generated by the first light source.

FIG. 4b shows a cross-sectional view of the lamp body of FIG. 2 and a light field generated by the second light source.

FIG. 9 shows a cross-sectional view of the lamp body of FIG. 2 as immovably attached to a ceiling.

DETAILED DESCRIPTION

Figure 36:
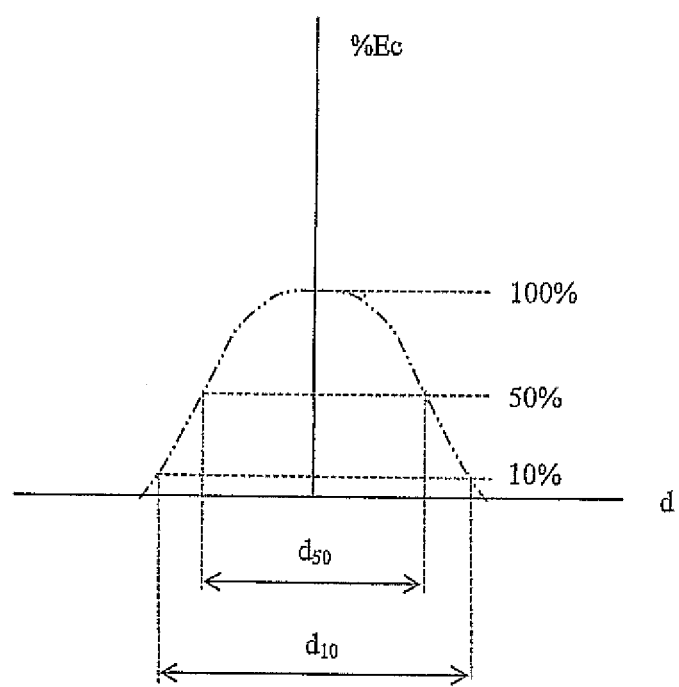

FIG. 1 shows a perspective view of a surgical lamp 1 that includes a lamp body 2 and a carrying system 3 (only a portion of a yoke of the carrying system 3 is shown). The surgical lamp 1 further includes a handle 4 that is positioned at and extends from (e.g., from an approximate center of) the lamp body 2. In alternative embodiments, the handle 4 may be positioned at another position along the lamp body 2. The surgical lamp 1 further includes multiple light sources (e.g., first light sources 5, second light sources 6, third light sources 7, and fourth light sources 8) and a control device 9 that are positioned along a surface of the lamp body 2. In the example embodiment of FIG. 1, the control device 9 is positioned along an edge portion of the lamp body 2. However, in alternative embodiments, the control device 9 may be provided in a housing that is separate from the lamp body 2 and/or at another position along the surgical lamp 1.

The surgical lamp 1 further includes a means 25 for triggering adjustment of respective light intensities of the light sources 5-8. Example means 25 include motion sensors and acceleration sensors that may be connected to the control device 9 for adjusting a resultant light field (e.g., an illuminated area of an operating site), as will be described in more detail below. For example, movement of the lamp body 2 may be detected by a motion sensor, and after completion of such movement, a respective signal may be provided (e.g., transmitted) to the control device 9. In some embodiments, movement of the lamp body 2 may be detected in a different manner (e.g. by evaluating signals provided by a distance measurement device). After completion of such movement, the control device 9 may adjust a resultant light field. In some embodiments, adjustment of the light intensities of the light sources 5-8 may be triggered manually (e.g., by using a sensor or releasing a switch).

The surgical lamp 1 further includes control units 28 for controlling respective light intensities of each light source 5-8 that is positioned along the lamp body 2. The carrying system 3 allows the lamp body 2 to be positioned (e.g., located and/or oriented) arbitrarily within a particular spatial region according to a predefined range of movement in order to optimally illuminate an operating site on a patient.

The light sources 5-8 include light-emitting diodes (LEDs) and optical devices (e.g., lenses) that bundle light beams emitted from the LEDs into sheaves of light. LEDs (e.g., white LEDs) that have different white color hues (e.g., warm white and cold white) can be used for achieving a suitable color temperature. Accordingly, a color temperature of light emitted from the surgical lamp 1 can be adjusted. In some embodiments, surgical lamps may include colored LEDs, which may allow for a larger range of adjustment of the color temperature than do white LEDs. In some embodiments, surgical lamps may include light sources that emit light beams of the same color temperature.

The light sources 5-8 utilize two different lenses to form the sheaves of light from the light beams emitted from the LEDs. The light sources 5, 7 use a first lens that has a relatively large diameter and accordingly provides light sheaves that generate small-diameter light fields. The light sources 6, 8 use a second lens that has a relatively small diameter and accordingly provides light sheaves that generate large-diameter light fields. In some embodiments, the light sources 5-8 use lenses that have the same diameter but that have different optical characteristics. For example, the lenses may generate light fields that have different light distributions and/or different light field diameters according to different optical effective faces of the lenses and/or different diameters of the lenses. In some embodiments, surgical lamps may include other means for generating light sheaves that provide light fields of different diameter, such as reflectors.

In the example lamp body 2, the first and second light sources 5, 6 are formed as structures that have fixed (e.g., non-adjustable) orientations with respect to a light-emitting surface 29 (shown in FIG. 2) of the lamp body 2. The third and fourth light sources 7, 8 are formed as structures (e.g., tiltable structures) that have adjustable orientations with respect to the light-emitting surface 29 of the lamp body 2. The orientations of the light sources 7, 8 may be adjustable individually or may be adjustable in groups that allow the light sources 7, 8 to be controlled by a common driving device 10. Using tiltable light sources along with non-tiltable light sources may advantageously allow for adjusting light field diameters at different distance from the lamp body 2. The light sources 5, 7 are similar in construction and function, with the exception that the light sources 5 are non-tiltable light sources (e.g., that have fixed orientations when attached to the lamp body 2), whereas the light sources 7 are adjustable (e.g., tiltable) light sources (e.g., that have adjustable orientations when attached to the lamp body 2). The light sources 6, 8 are similar in construction and function, with the exception that the light sources 6 are non-tiltable light sources (e.g., that have fixed orientations when attached to the lamp body 2), whereas the light sources 8 are adjustable (e.g., tiltable) light sources (e.g., that have adjustable orientations when attached to the lamp body 2). While the lamp body 2 includes the light sources 5-8, in some embodiments, a lamp body of a surgical lamp includes the first and second light sources 5, 6 but does not include the third and fourth light sources 7, 8.

The first and second light sources 5, 6 are positioned along the lamp body 2 (e.g., along the light-emitting surface 29 of the lamp body 2) in an arrangement that forms a spherical surface that has a radius of about 1300 mm. In alternative embodiments, the light sources 5, 6 may be positioned in an arrangement that does not form a surface, in an arrangement that forms a non-spherical surface, or in an arrangement that forms a spherical surface that has a different radius.

The control device 9 controls the light intensities of the individual light sources 5-8 and is connected to the light sources 5-8 via respective control units 28. The control device 9 further controls tilting angles of the light sources 7, 8 via the driving device 10.

FIG. 2 shows a perspective view of the lamp body 2 without the handle 4 shown in FIG. 1. The lamp body 2 has a light-emitting surface 29 that includes an inner area I (e.g., a circular area) and an outer area II positioned adjacent (e.g., around) the inner area I. The first and second light sources 5, 6 are mounted to the lamp body 2 along the inner area I, and the third and fourth light sources 7, 8 are mounted to the lamp body 2 along the outer area II. Accordingly, the light sources 7, 8 are spaced farther from an optical axis 11 (shown in FIGS. 4a-4e) of the lamp body 2 than are the light sources 5, 6.

FIGS. 3a-3e show graphs of light distributions generated by the light sources 5, 6. The light field diameters of the light fields may be changed in order to achieve a desired resultant light field diameter by controlling light sources of the lamp body 2, as will be discussed in more detail below.

FIGS. 3a and 3b show graphs of light distributions generated by the first and second light sources 5, 6, respectively. The light distributions are provided as a percent of central illuminance (Ec) (i.e., relative central illuminance) as a function of a light field diameter (d). The light distributions conform with standard light fields generated by a surgical lamp. For example, the light distributions conform with the DIN EN 60601-2-41:2010 standard (i.e., the light fields have a central illuminance Ec of 100%). The light field diameter (d10) is defined as a diameter of a circle around the center of the light field where the illuminance is 10% of the central illuminance Ec. The light field can also be characterized by a diameter d50 of a circle around the center of the light field where the illuminance is 50% of the central illuminance Ec. According to the DIN EN 60601-2-41:2010 standard, the diameter d50 is at least half of the light field diameter d10 at a distance of 1000 mm from the light-emitting surface 29, as shown by the light distributions in FIGS. 3a and 3b.

The relative central illuminances of 10%, 50%, and 100% are indicated by dashed horizontal lines. The light field diameter d10 and the diameter d50 can be determined by intersecting the dashed horizontal lines with the line that represents the light distribution. As shown in the graphs, the light fields conform to the standard in that the diameter d50 is larger than half of the light field diameter d10.

FIG. 3c shows a graph of a light distribution (shown in solid line) resulting from a superposition of the light distributions of FIGS. 3a (shown in dash-dot line) and 3b (shown in dash-double-dot line) according to the diameter d of the light fields. As shown in FIG. 3c, the light field diameter d10 of the first light source 5 is less than the light field diameter d10 of the second light source 6. Furthermore, 100% of the central illuminance Ec of each light source 5, 6 is equal to 50% of the central illuminance Ec of the resultant light field.

FIG. 3c also shows a relative illuminance (x %) of the central illuminance Ec. Accordingly, the diameter dx is defined as a diameter of a circle around the center of the light field center where the illuminance is x % of the central illuminance (Ecx). In some examples, Ecx may be provided as a factory preset value, such that the diameter dx is also provided as a factory preset value that remains constant as a result of controlling the light sources 5-8. Typically, the light field diameter d10 is selected as the diameter dx. In some examples, Ecx is determined by a user.

FIG. 3d shows a graph of a light distribution resulting from a superposition of light distributions different from those of FIGS. 3a and 3b. Such light distributions may result from controlling (e.g., adjusting) the central illuminances Ec of the individual light sources 5, 6. For example, the central illuminance Ec of the smaller-diameter light field (shown in dash-double-dot line) is less than that of the corresponding light distribution shown in FIG. 3c. Furthermore, the central illuminance Ec of the larger-diameter light field (shown in dash-dot-line) is greater than that of the corresponding light distribution shown in FIG. 3c. As shown in the graphs of FIGS. 3c and 3d, the resultant light fields conform with the standard in that the diameter d50 is larger than half of the light field diameter d10.

FIG. 3e shows graphs of the light field distributions of FIG. 3c (shown in dashed line) and FIG. 3d (shown in dotted line). As shown in FIG. 3e, the diameters d10 of the resultant light fields decrease when the central illuminance Ec is increased by the light source generating the smaller light field diameter d10 and/or when the central illuminance Ec is reduced by the light source generating the larger light field diameter d10.

Accordingly, the light field diameters d10 of the resultant light fields increase when the central illuminance Ec is reduced by the light source generating the smaller light field diameter d10 and/or when the central illuminance Ec is increased by the light source generating the larger light field diameter d10. In order to maintain the central illuminance Ec of the resultant light field at a constant value, the central illuminance Ec of one of the light sources can be reduced by about the same amount as the that which the central illuminance Ec of the other light source is increased so that the sum of the individual central illuminances Ec remains constant.

FIGS. 4a-4d show cross-sectional views of the lamp body 2 (along the line A-A in FIG. 1) and light fields generated by the light sources 5-8. It should be understood that the lines illustrating the light sheaves are not drawn to scale or to a particular orientation and therefore do not define exact boundaries of a bright-dark-limit. Furthermore, illustration of the different diameters does not define exact boundaries of a bright-dark-limit because when the diameter is defined as the light field diameter d10, light that has an intensity corresponding to less than 10% of the central illuminance Ec (e.g., scattered light) can be transmitted outside of this diameter.

Figure 4C:
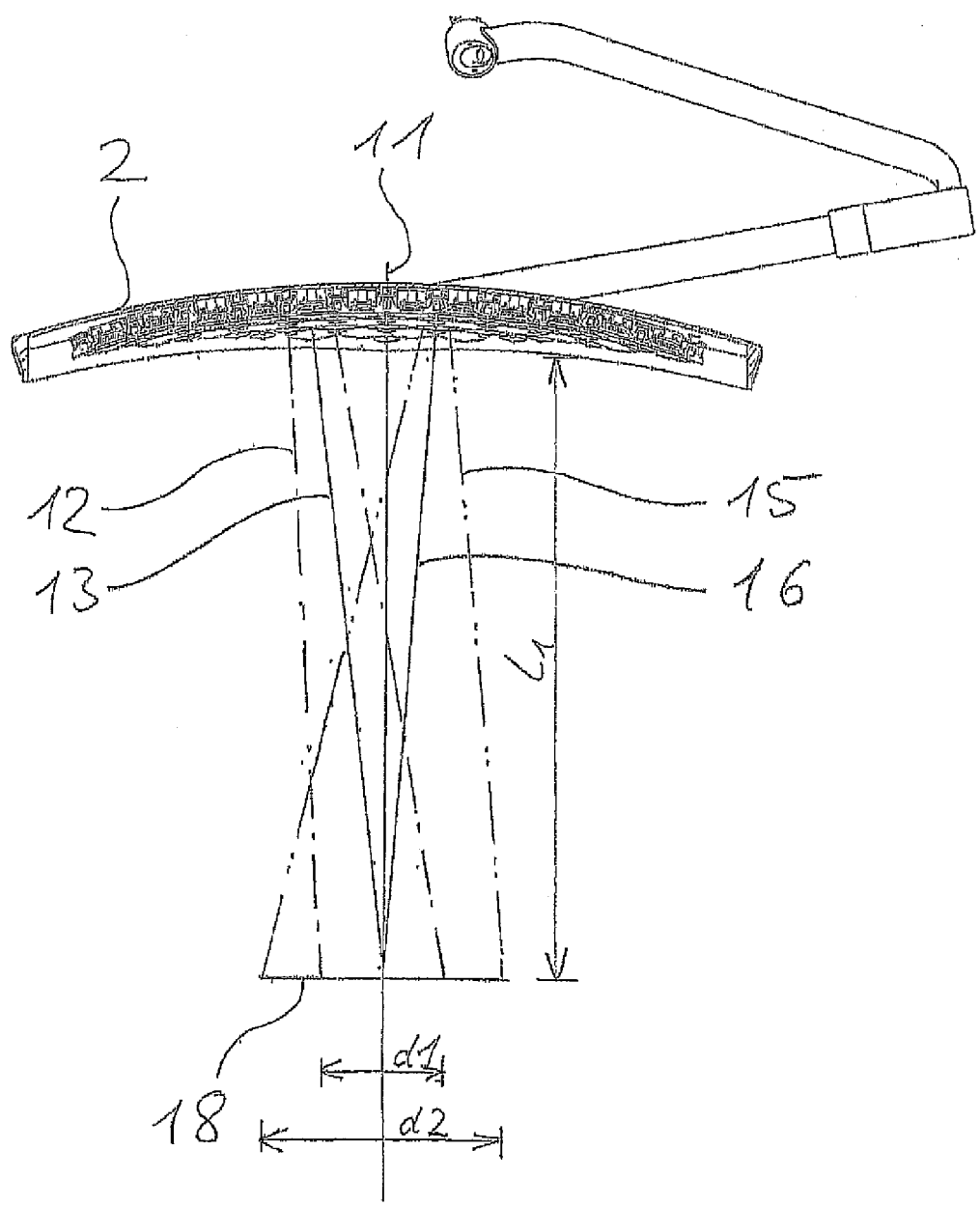
FIG. 4c shows a cross-sectional view of the lamp body of FIG. 2 and a resultant light field generated by the first and second light sources.

Referring to FIG. 4a, the lamp body 2 has an optical axis 11 that defines a center of a light field that is generated by the lamp body 2. Each light source 5 radiates a light sheaf 12 (shown in dash-dotted lines; only one light sheaf 12 shown for clarity). The light sheaf 12 has an axis 13 that intersects the optical axis 11 of the lamp body 2 at a distance L1 from the lamp body 2. The light sources 5 are arranged across the light-emitting surface 29 of the lamp body 2 such that all of the axes 13 of the light sheaves 12 intersect the optical axis 11 at the same point, thereby generating a first light field 14 on the operating site at the distance L1. In the example of FIGS. 4a-4d, the distance L1 is about 1300 mm. However, in other embodiments, L1 may be a different value, depending on the application and the size of the lamp body. The light field diameter d10 of the light field 14 is denoted as d1 in FIG. 4a.

Referring to FIG. 4b, each light source 6 radiates a light sheaf 15 (shown in dash-double-dotted-lines; only one light sheaf 15 shown for clarity). The light sheaf 15 has an axis 16 that intersects the optical axis 11 of the lamp body 2 at the distance L1 from the lamp body 2. The light sources 6 are arranged across the light-emitting surface 29 of the lamp body 2 such that the axes 16 of the light sheaves 15 intersect the optical axis 11 at the same point, thereby generating a second light field 17 on the operating site at the distance L1. The light field diameter d10 of the light field 17 is denoted as d2 in FIG. 4b. As discussed above with respect to FIG. 3c, the light field diameter d2 of the second light field 17 generated by the second light sources 6 is greater than the light field diameter d1 of the first light field 14 generated by the first light sources 5.

FIG. 4c shows the light sheaves 12 and 15 as superimposed on one another to generate a resultant light field 18 on the operating site that is located at the distance L1 from the lamp body 2.

Figure 4D:
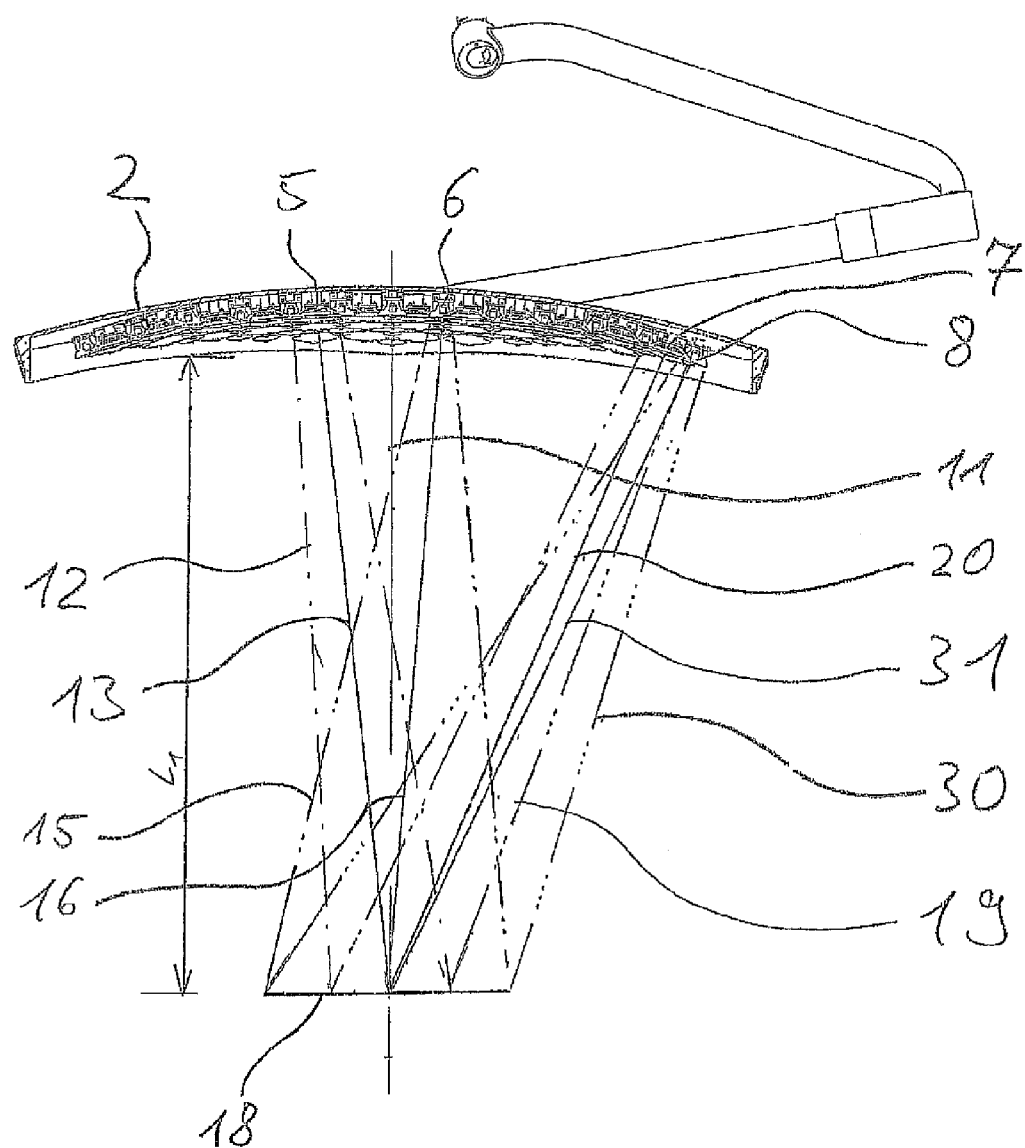
FIG. 4d shows a cross-sectional view of the lamp body of FIG. 2 and a resultant light field generated by the first and second and third and fourth light sources at a distance L1 from the lamp body.

Referring to FIG. 4d, each light source 7 radiates a light sheaf 19 (shown in dash-triple-dotted-lines; only one light sheaf 19 shown for clarity). The light sheaf 19 has an axis 20 that intersects the optical axis 11 of the lamp body 2 at the distance L1 from the lamp body 2. The light sources 7 are arranged across the light-emitting surface 29 of the lamp body 2 such that the axes 20 of the light sheaves 19 intersect the optical axis 11 of the lamp body at the same point.

Still referring to FIG. 4d, each light source 8 radiates a light sheaf 30 (shown in dash-quadruple-dotted lines; only one light sheaf 30 shown for clarity). The light sheaf 30 has an axis 31 that intersects the optical axis 11 of the lamp body 2 at the distance L1 from the lamp body 2. The light sources 8 are arranged across the light-emitting surface 29 of the lamp body 2 such that the axes 31 of the light sheaves 30 intersect the optical axis 11 of the lamp body 2 at the same point. The light sources 7, 8, are adjustable (e.g., tiltable) with respect to the light-emitting surface 29 of the lamp body 2 such that the axes 20, 31, respectively, can intersect the optical axis 11 at the same point as do the axes 13, 16 of the light sheaves 12, 15, respectively. The third light sheaf 19 generates a light field having a diameter that is smaller than that of the fourth light sheaf 30. Together with the light sheaves 12, 15, the light sheaves 19, 30 generate the resultant light field 18. In this manner, the smaller-diameter light fields (i.e., generated by the light sheaves 12, 19) and the larger-diameter light fields (i.e., generated by the light sheaves 15, 30) are superposed to generate the light field 18.

Figure 4E:
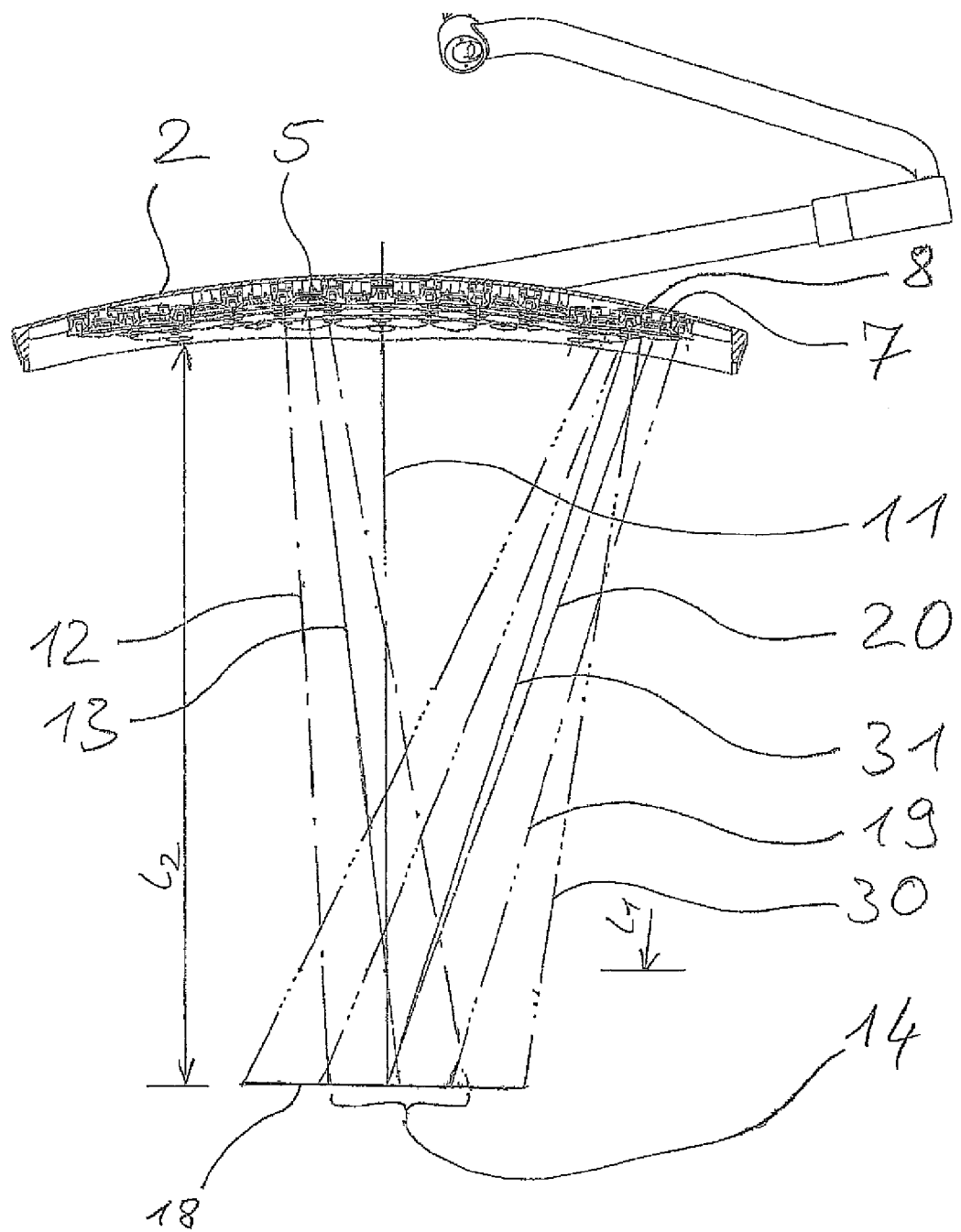
FIG. 4e shows a cross-sectional view of the lamp body of FIG. 2 and a resultant light field generated by the first, second, third, and fourth light sources at a distance L2 from the lamp body.

FIG. 4e shows a cross-sectional view of the lamp body 2 and a light field that is generated at a distance L2 that is larger than the distance L1. While a light field 14 generated by a single light sheaf 12 is not concentric with the optical axis 11 of the lamp body 2 because its axis 13 does not intersect the optical axis 11 at the distance L2, the superposition of several light sheaves 12 emitted from respective light sources 5 distributed about a circumference of the lamp body 2 collectively form a light field 14 that, is concentric with the optical axis 11.

The third and fourth light sources 7, 8 are tiltable by the control device 9 via the driving device 10 such that the axes 20, 31 of the light sheaves 19, 30 intersect the optical axis 11 at the distance L2. When the distance is changed due to movement of the lamp body 2, the third and fourth light sources 7, 8 can be tilted again such that the axes 20, 31 intersect the optical axis 11 of the lamp body at the actual distance of the operating site.

Figure 5:
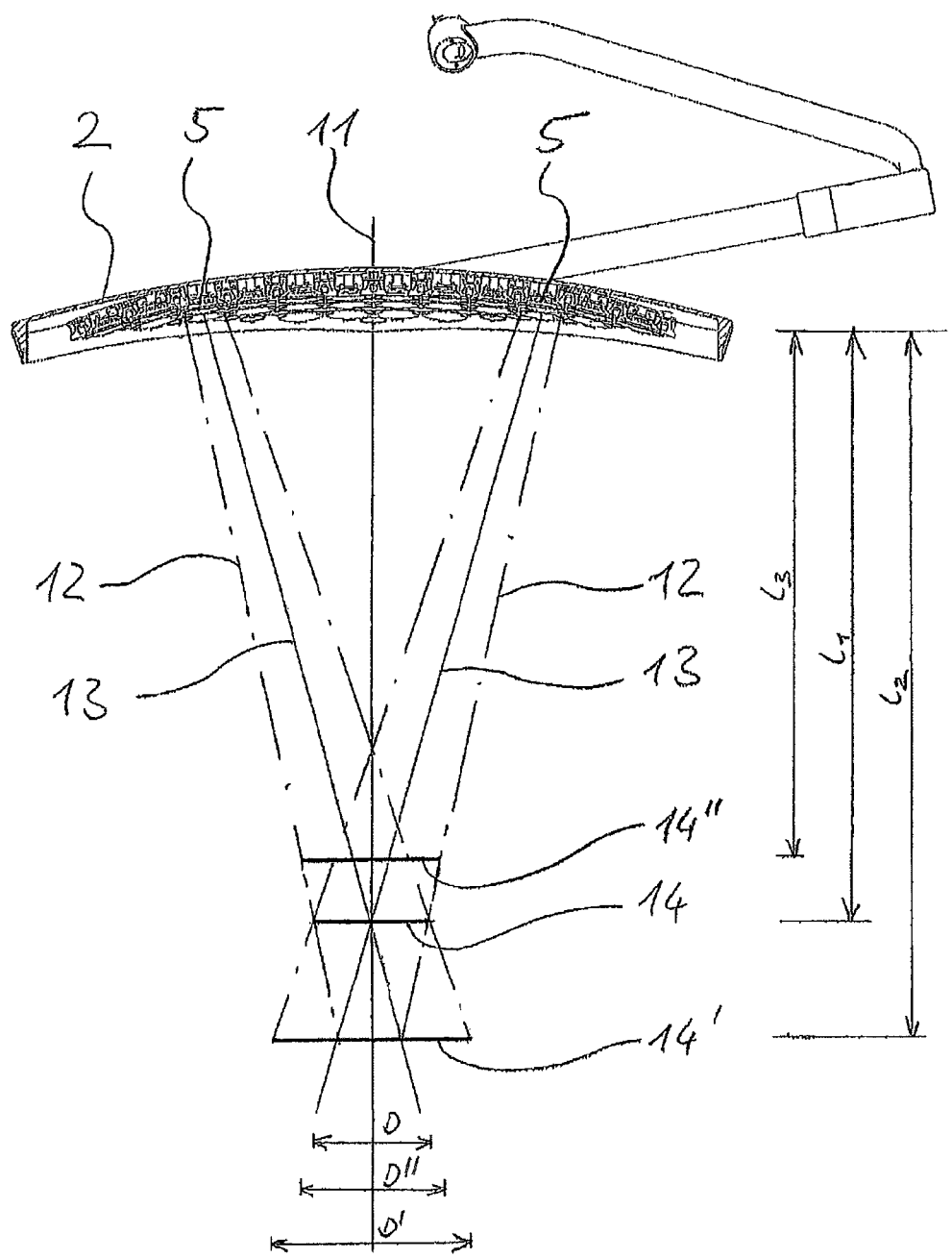
FIG. 5 shows a cross-sectional view of the lamp body of FIG. 2 and three different light fields generated by two of the first light sources.

FIG. 5 shows a cross-sectional view of the lamp body 2 and three light fields 14, 14', 14" generated by two of the first light sources 5. The light fields 14, 14', and 14" are generated on operating sites at the distances L1, L2, and L3, respectively, and are centered at the optical axis 11 of the lamp body 2. The axes 13 of the light sheaves 12 radiated from the light sources 5 intersect the optical axis 11 at the distance L1 to generate the light field 14 on the operating site.

The light fields 14, 14', 14" have diameters D, D', D", respectively, that depend on the distance of the operating site from the lamp body 2. The light field 14 generated on the operating site at the distance L1 (i.e., where the axes 13 intersect the optical axis 11) has the smallest diameter (D). Changing the distance of the operating site to, for example, L2 or L3, generates the light fields 14', 14" that have diameters (D', D") larger than that of the light field 14. In the example of FIG. 5, the diameters D, D', D" are illustrated fundamentally and therefore do not represent the light field diameters d10 or the diameters dx corresponding to a relative central illuminance Ecx of the light fields 14, 14', 14". Accordingly, the example of FIG. 5 shows that the diameter of a light field changes as the distance between the lamp body 2 and the operating site changes. As a result, the light field diameter d10, as well as the diameter dx corresponding to the relative central illuminance Ecx, changes as such distance changes.

In order to prevent the light field diameter d10 or the diameter dx from increasing when the distance changes from L1 to L2 or L3, the light source 5 generating the light field with the smaller light field diameter d1 (shown in FIG. 4a) is controlled such that its light intensity increases, and/or the light source 6 generating the light field with the larger light field diameter d2 (shown in FIG. 4b) is controlled such that its light intensity decreases. Conversely, in order to prevent the light field diameter d10 or the diameter dx from decreasing when the distance changes from L2 or L3 to L1, the light source 5 is controlled such that its light intensity decreases, and/or the light source 6 is controlled such that its light intensity increases. Controlling the light sources 5, 6 such that the light field diameter d10 remains constant accordingly maintains the central illuminance Ec of the light field at a constant value.

Figure 6:
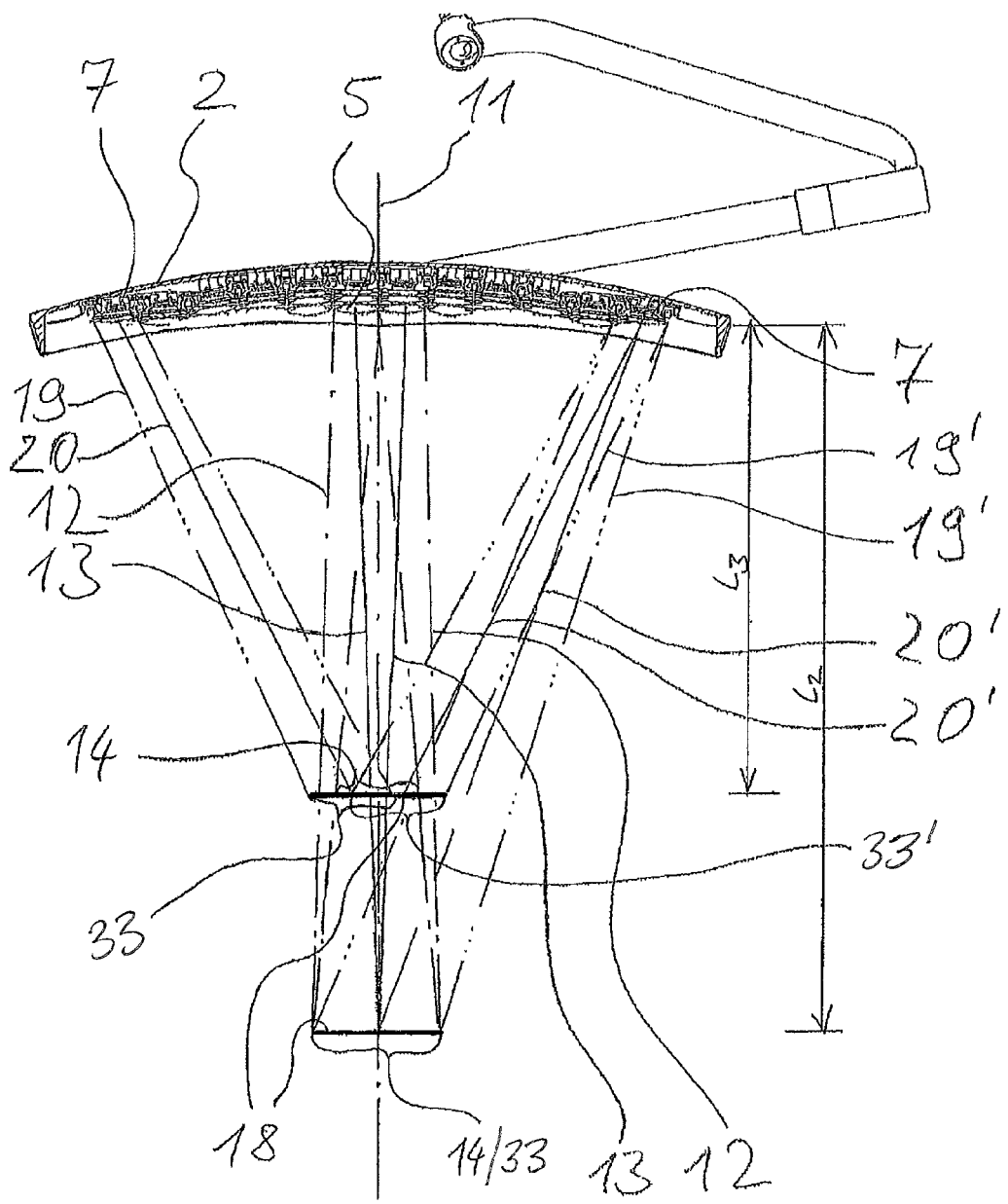
FIG. 6 shows a cross-sectional view of the lamp body of FIG. 2 and light fields generated by the first and third light sources.

FIG. 6 shows a cross-sectional view of the lamp body 2 and light fields generated by the first and third light sources 5, 7. As discussed above, the first light sources 5 are non-tiltable light sources, and the third light sources 7 are tiltable light sources. The third light sources 7 are tiltable about a tilting axis that is tangent to a circle about the optical axis 11 of the lamp body 2. In some embodiments, several third light sources 7 are attached to a holder (not shown) that is mounted to the lamp body 2 and that is tiltable about the tiling axis via a common driving device 10. In some embodiments, the light sources 7 are alternatively or additionally attached separately to the lamp body 2 and therefore individually tiltable about the tilting axis via respective driving devices 10. The majority or all of the first light sources 5 are positioned within the inner area I (shown in FIG. 2) of the lamp body 2. The majority or all of the third light sources 7 are positioned within the outer area II (shown in FIG. 2) of the lamp body 2.

The light fields 14, 33 generated by the light sources 5, 7, respectively, are similar and have light field diameters that are substantially equal on the operating site. In the example of FIG. 6, only two light sheaves 12 generated by respective light sources 5 and two light sheaves 19, 19' generated by respective light sources 7 are shown for clarity. For exemplary purposes and for clarity, one light sheaf 19' is tilted to form the light field 33' at the distance L3, while the other light sheaf 19' is tilted to form (e.g., along with the light field 14) the resultant light field 18 at the distance L2.

The light sources 5, 7 are arranged across the light-emitting surface 29 of the lamp body 2 such that the axes 13, 20, 20' of the light sheaves 12, 19, 19' intersect the optical axis 11 of the lamp body 2 at the same respective points to generate the light fields 14, 33, 33'. The light field 18 results from the superposition of the light fields 14 and 33, 33'. Depending on the desired application, such a light field has a corresponding light distribution that conforms with the standard of surgical lamps. As a result, a preset relative central illuminance Ecx is generated at a predetermined diameter dx. In the example of FIG. 6, the control device 9 is configured to individually control the light intensities of the respective light sources 5, 7 and to control tilting angles of the third light sources 7. Accordingly, the preset relative central illuminance Ecx can be generated at the predetermined diameter dx at a chosen distance.

The surgical lamp 1 is designed to have minimum and maximum working distances (i.e., the distances between the lamp body 2 and the operating site) determined by a working range that complies with standardized requirements.

In order to maintain the predetermined diameter dx at a constant value when the working distance changes, the control device 9 is operated to control the tilting angles of the third light sources 7 such that the third light field 33 shifts radially with respect to the optical axis 11 of the lamp body 2. Furthermore, the light intensities of the first and third light sources 5, 7 are also controlled by the control device 9. As compared to the position of the light sources 7 when the resultant light field 18 is generated at the shorter distance L3, the light sources 7 are tilted radially away from the optical axis 11 when the resultant light field 18 is generated at the larger distance L2. The light intensities of the light sources 5, 7 and the angles of the light sources 7 may be controlled in any order to maintain the predetermined diameter dx at a constant value.

In some examples, the axes 13, 20, 20' of all of the respective light sheaves 12, 19, 19' may not be directed to the exact same point along the optical axis 11 of the lamp body 2. For example, some of the axes 13, 20, 20' may be directed to the same point along the optical axis 11 (e.g., directed to a point that is close to the intended point along the optical axis 11). In some examples, the tilting angles and the relative central illuminances Ecx of all of the light sources 5, 7 are empirically determined for respective predetermined diameters dx for operating sites at different working distances.

In some examples, the central illuminance Ec may be maintained at a constant value by operating the control device 9 to control the light intensities of the individual light sources 5, 7 and the tilting angles of the light sources 7.

In some examples, the minimum allowable predetermined diameter dx may be maintained at a constant value over the entire working range by controlling the light sources 5, 7 such that the predetermined diameter dx of the resultant light field 18 generated at the maximum working distance is no larger than the minimum allowable predetermined diameter dx. This means that in a case where the predetermined diameter dx equals the light field diameter d1, the light sources 5, 7 are configured (e.g., designed and arranged) such that the light field diameters d1 of the individual light fields 14, 33, 33' (and therefore, the resultant light field 18) generated at the maximum working distance are no larger than the minimum allowable predetermined light field diameter d1.

In an alternative embodiment, the light sources 5, 7 can also be configured (e.g., designed and arranged) such that the predetermined diameter dx of the resultant light field 18 generated at a distance larger than the maximum working distance is no larger than the minimum allowable predetermined diameter dx. Accordingly, in the case where the predetermined diameter dx equals the light field diameter d1, the light field diameter d1 of the individual light fields generated at the maximum working distance is no larger than the minimum allowable predetermined light field diameter d1.

Figure 7:
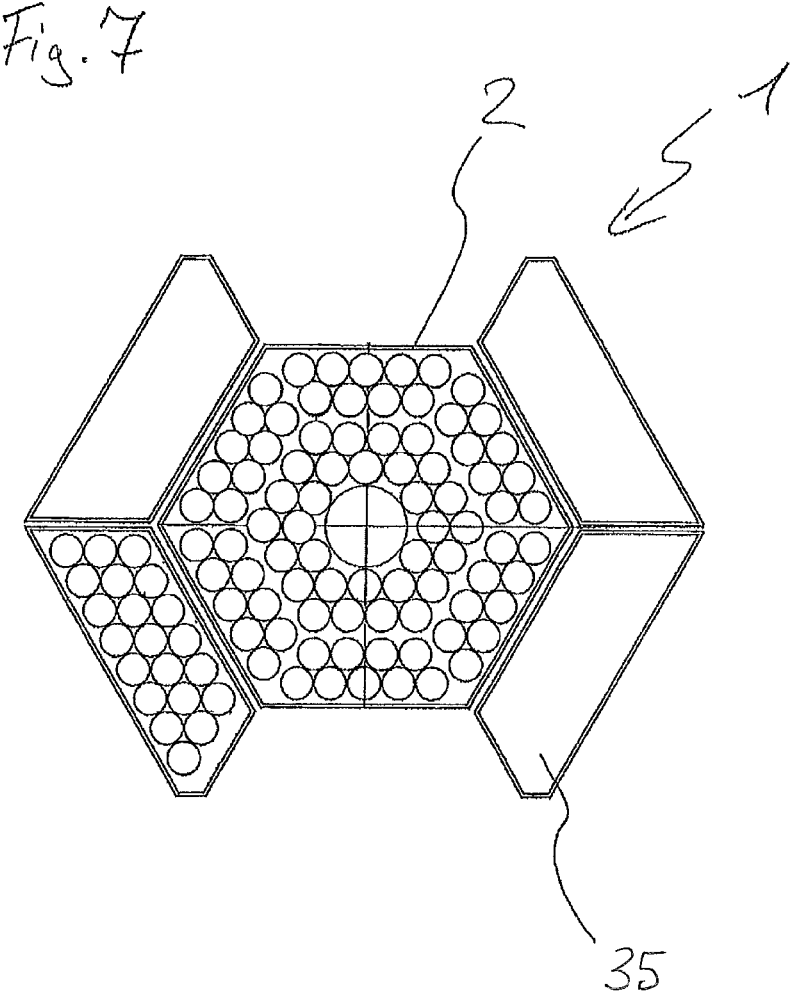
FIG. 7 shows a bottom view of a portion of the surgical lamp of FIG. 1 with attachment modules.

FIG. 7 shows a bottom view of a portion of the surgical lamp 1 as engaged with attachment modules 35. The lamp body 2 includes lateral interfaces (e.g., electrical and mechanical interfaces) to which the attachment modules 35 are attached. In some embodiments, the interfaces are provided as a standard feature. The attachment modules 35 can provide various functionalities. In the example of FIG. 7, the attachment modules 35 are provided with light sources 5 (shown in only one attachment module 35). However, in some embodiments, the attachment modules 35 may additionally or alternatively include any of the other light sources 6-8. In some embodiments, the attachment modules 35 may be provided with additional light sources (e.g., narrow-band light sources for fluorescence excitation) or other elements, (e.g., sensors or cameras).

Figure 8:
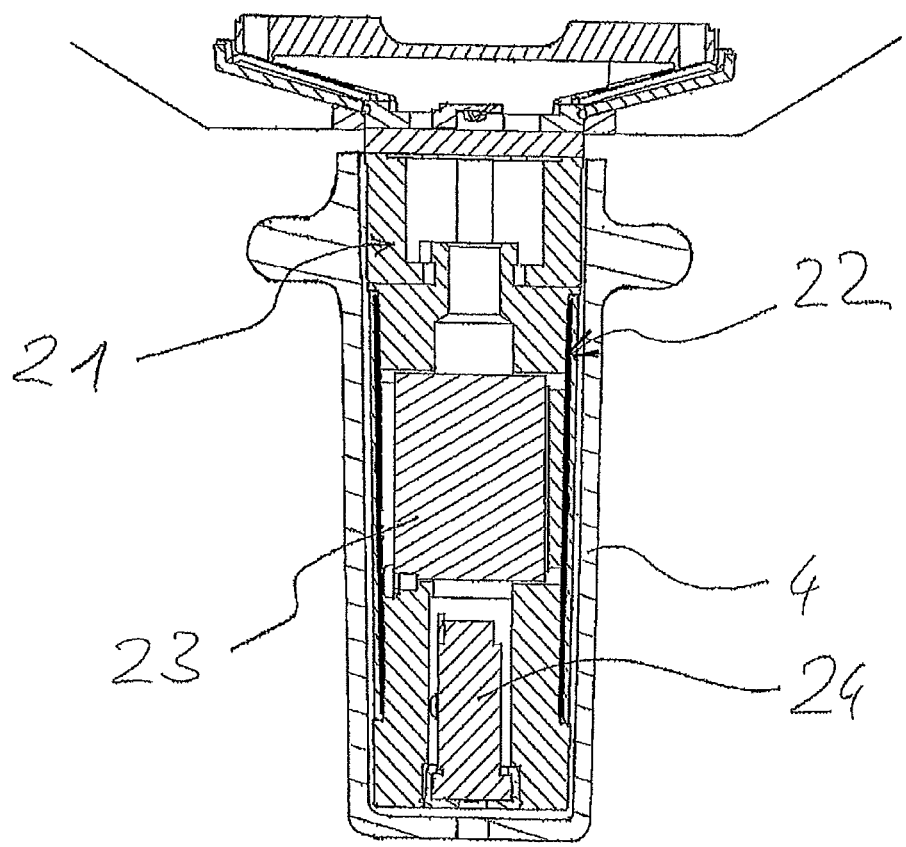
FIG. 8 shows a handle of the surgical lamp of FIG. 1 engaged with a handle retainer.

FIG. 8 shows a cross-sectional view of the handle 4 as attached to the surgical lamp 1. The handle 4 is engaged with (e.g., placed over) a handle retainer 21 of the surgical lamp 1 in a fixed manner via a latch mechanism (not shown). The surgical lamp 1 further includes an operating device that is positioned adjacent the handle retainer 21. The operating device includes at least one sensor 22 that receives input and an evaluation unit 23 that provides for contactless operation of the surgical lamp 1 (e.g., operation of the surgical lamp 1 without touching the sensor 22 or other portions of the operating device). Other components (e.g., sterile components of the lamp body 2, such as the handle 4) may, however, be touched by a user (e.g., a surgeon).

The user may set the desired diameter dx and the desired central illuminance Ec using the operating device. For example, a user may set the diameter dx by dragging a finger along the handle 4 in an axial direction or set the central illuminance Ec by dragging a finger along a circumference of the handle 4. Accordingly, the diameter dx and the central illuminance Ec may be set in a stepless manner (e.g., adjusted to any value within an allowable range). However, in other embodiments, the desired diameter dx and central illuminance Ec may be set using other setting elements (e.g., push or turn switches, control dials with sterile operating knobs, or the like). In some embodiments, selectable preset diameters dx and/or selectable preset central illuminances Ec may be provided.

Still referring to FIG. 8, the surgical lamp further includes a device 24 disposed within the handle retainer 21. The device 24 detects the distance between the lamp body 2 and the operating site. Accordingly, the device 24 is formed as a distance sensor (e.g., a laser sensor). Alternatively, the surgical lamp may include other types of distance measuring devices (e.g., ultrasonic sensors or angle detectors disposed in the carrying system 3) for determining the position of the lamp body 2 or the distance between the lamp body 2 and the operating site.

The values of the light intensities of the individual light sources 5-8 and the tilting angles of the third and fourth light sources 7, 8 are empirically determined and depend on the desired diameter dx (e.g., the light field diameter d10), the central illuminance Ec of the surgical lamp 1, and the working distance between the lamp body 2 and the operating site. The values of the light intensities and the tilting angles may be stored in a mapping in a storage of the control device 9. The values conform to the standard for surgical lamps such that the diameter d50 and the light field diameter d10 can be achieved according to acceptable ratios. Alternatively or additionally, relationships between the individual values can be stored in the mapping in the storage of the control device 9.

Any of the light sources 5-8 may be grouped together such that their light intensities can be collectively controlled by one control unit 28. The light sources 5-8 may be grouped according to the light field diameter d10 of the generated light field or the distance of the light sources 5-8 from the optical axis 11 of the lamp body 2 (e.g., positioning of the light sources 5-8 along the inner area I or the outer area II). Within the inner and/or outer areas I, II, the light sources 5-8 may be further grouped (e.g., based on the color temperature of the LEDs).

In operation, the device 24 (i.e., the laser sensor) measures the distance between the lamp body 2 and the operating site, and initial target values for the diameter dx corresponding to the preset relative central illuminance Ecx and for the central illuminance Ec for generating the resultant light field 18 are set for the surgical lamp 1 by the control device 9. Such values may be altered or set via the operating device. The control device 9 controls the light intensities of the light sources 5-8 and the driving device 10 of the tiltable light sources 7, 8 to achieve the values. The values are retrieved from the storage of the control device 9 and set as the operating data of the surgical lamp 1.

A change in the position and/or orientation of the lamp body 2 (i.e., a change in the working distance) is detected by the means 25 (e.g., a motion sensor or an acceleration sensor) for triggering adjustment of the light intensities of the individual light sources 5-8 for adjusting the light field. Following the movement of the lamp body 2, the distance between the lamp body 2 and the operating site is measured by the device 24 (e.g., laser sensor) or, alternatively, detected in another manner. According to the detected value of the movement of the lamp body 2, the diameter dx and the central illuminance Ec of the surgical lamp 1 are corrected by retrieving the corresponding operating data from the storage of the control device 9. The light sources 5-8 (individually and/or in groups) are controlled by the control device 9 with an appropriate mixing ratio according to force values of currents. Furthermore, the driving device 10 is controlled to adjust the predetermined tilting angles. As a result of this correction, the diameter dx and/or the central illuminance Ec of the operating field remains constant following movement of the lamp body 2.

In the example surgical lamp 1, the lamp body 2 is formed as a single housing and optionally includes non-tiltable attachment modules 35 to which all of the light sources 5, 6 are mounted. However, in certain embodiments, a surgical lamp may include a lamp body that is formed from multiple housings. The multiple housings may be designed as modules to which multiple light sources 5, 6 may be attached. In such an embodiment, the multiple housings can be tilted with respect to each other such that the outer light sources 5, 6 may be tilted to direct their axes 13, 16 to desired intersection points on the optical axis of the lamp body.

In some embodiments, the lamp body 2 of the surgical lamp 1 may be rigidly attached within a room. For example, FIG. 9 shows the lamp body 2 as immovably attached to a room ceiling. In alternative embodiments, the light sources and other elements are attached directly to the room ceiling, which, in such cases, serves as a lamp body.

In the example of FIG. 9, the lamp body 2 has an optical axis 38 (e.g., a tiltable optical axis) along which the resultant light field 18 is generated. The optical axis 38 does not have a fixed orientation relative to the lamp body 2. Instead, an angle between the optical axis 38 and the lamp body 2 is defined by light beam sheaves emitted from fifth light sources 26. In contrast to the first light sources 5 that are non-tiltable within the lamp body 2, the fifth light sources 26 are tiltable within the lamp body 2. Thus, the fifth light sources 26 can be adjusted to change the position of the tiltable optical axis 38 of the lamp body 2, and the resultant light field 18 generated by the light sources 26 can illuminate an arbitrary region (e.g., an area of a surgical table).

In the example embodiment of FIG. 9, the lamp body 2 further includes sixth light sources 27 that are also tiltable within the lamp body 2. The sixth light sources 27 are controlled by the control device 9 to achieve the same tilting movements with respect to the tiltable optical axis 38 as those of the third light sources 7 with respect to the optical axis 11.

The lamp body 2 of FIG. 9 includes a device to detect the distance along the optical axis 38 between the lamp body 2 and the operating site for maintaining a constant value of the predetermined diameter dx of the resultant light field and, optionally, for maintaining a constant value of the central illuminance Ec as the distance changes.

A number of embodiments have been described. Nevertheless, it will be understood that various modifications may be made without departing from the spirit and scope of the disclosure. Accordingly, other embodiments are within the scope of the following claims.

What is claimed is:

1. A surgical lamp for illuminating an operating site, comprising:

a lamp body having an optical axis and comprising a first light source and a second light source that respectively generate a first light field and a second light field on the operating site, wherein the operating site is located at a particular distance from the lamp body, and the first and second light fields together produce a resultant light field, wherein the resultant light field has a circular shape and is associated with a light distribution that conforms with a surgical lamp standard, such that a preset relative central illuminance (Ecx) of the light distribution is generated at a predetermined diameter (dx) of the resultant light field;

a control device configured to control a first light intensity of the first light source and a second light intensity of the second light source, such that the preset relative central illuminance (Ecx) is generated at the predetermined diameter (dx) at the particular distance; and a device for detecting a distance between the lamp body and the operating site, wherein the control device is configured to control the first and second light intensities of the first and second light sources, respectively, such that the predetermined diameter (dx) of the resultant light field on the operating site is maintained at a substantially constant value as the distance between the lamp body and the operating site changes, wherein the first and second light sources are respectively assigned to first and second groups of light sources according to one or more criteria comprising diameters of light fields generated by light sources within the first and second groups of light sources and distances of the light sources within the first and second groups of light sources from the optical axis, wherein the control device is configured such that the light sources within the first and second groups of light sources can be controlled similarly and such that the first and second groups of light sources can be controlled independently of one another, and wherein the control device comprises a storage that stores a mapping, and wherein light intensities of the light sources in the first and second groups of light sources are stored as values associated with currents in the mapping, such that the values are retrievable by the control device in a mixing ratio that depends on the distance between the lamp body and the operating site.

2. The surgical lamp according to claim 1, further comprising a means for triggering adjustment of light intensities of light sources of the lamp body.

3. The surgical lamp according to claim 2, wherein the lamp body comprises:

a light-emitting surface that is divided into an inner area (I) that has a circular shape and at least one outer area (II) positioned adjacent the inner area (I), wherein the first and second light sources are positioned along the inner area (I) and have first and second orientations, respectively, that are fixed with respect to the light-emitting surface;

a third light source and a fourth light source that respectively generate a third light field and a fourth light field having different diameters, the third and fourth light fields together with the first and second light fields generating the resultant light field, wherein the third and fourth light sources are positioned along the at least one outer area (II) and are tiltable with respect to the light-emitting surface of the lamp body; and a driving device for respectively tilting the third and fourth light sources to a third tilting angle and a fourth tilting angle, wherein the control device is configured to control a third light intensity of the third light source, a fourth light intensity of the fourth light source, and the driving device, such that the predetermined diameter (dx) of the resultant light field on the operating site is maintained at a substantially constant value as the distance between the lamp body and the operating site changes.

4. The surgical lamp according to claim 3, wherein the means for triggering adjustment of the light intensities comprises a motion sensor, and the control device is configured to evaluate a detected distance between the lamp body and the operating site, such that the control device appropriately controls the first, second, third, and fourth light sources following detection of a completed motion of the lamp body by the motion sensor.

5. The surgical lamp according to claim 1, wherein the control device is configured to ensure that a central illuminance (Ec) of the resultant light field conforms to the surgical lamp standard as the distance changes.

6. The surgical lamp according to claim 1, wherein at least one of the first and second light sources is tiltable with respect to a light-emitting surface of the lamp body.

7. The surgical lamp according to claim 1, further comprising modules to which at least one of the first and second light sources is attached, wherein the modules are tiltable with respect to each other.

8. The surgical lamp according to claim 1, wherein the first light source comprises a first lens and the second light source comprises a second lens, and wherein the first and second lenses have different optically effective surfaces configured to generate light fields that have different light distributions.

9. The surgical lamp according to claim 1, wherein the first light source comprises a first lens and the second light source comprises a second lens, and wherein the first and second lenses have different diameters.

10. The surgical lamp according to claim 1, further comprising an input means connected to the control device for setting the predetermined diameter (dx) at which the preset relative illuminance (Ecx) of the resultant light field is generated.

11. The surgical lamp according to claim 10, wherein the input means comprises a means for selecting among different preset predetermined diameters (dx) at which the preset relative illuminance (Ecx) is generated.

12. The surgical lamp according to claim 1, wherein the surgical lamp standard is DIN EN 60601-2-41:2010.

13. The surgical lamp according to claim 1, wherein one or more of the light sources are tiltable with respect to a light-emitting surface of the lamp body, and tilting angles of the one or more light sources depend on the distance between the lamp body and the operating site, and wherein the tilting angles are stored in the storage of the control device and are retrievable by the control device according to the distance between the lamp body and the operating site.

14. A method for operating a surgical lamp, comprising:
detecting a change in a distance between a lamp body of the surgical lamp and an operating site, wherein the lamp body has an optical axis and comprises a first light source and a second light source that respectively generate a first light field and a second light field on the operating site, wherein the operating site is located at a particular distance from the lamp body, and the first and second light fields together produce a resultant light field, wherein the resultant light field has a circular shape and is associated with a light distribution that conforms with a surgical lamp standard, such that a preset relative central illuminance (Ecx) of the light distribution is generated at a predetermined diameter (dx) of the resultant light field, wherein the surgical lamp further comprises a control device configured to control a first light intensity of the first light source and a second light intensity of the second light source, such that the preset relative central illuminance (Ecx) is generated at the predetermined diameter (dx) at the particular distance, wherein the surgical lamp further comprises a device for detecting the distance between the lamp body and the operating site, and wherein the control device is configured to control the first and second light intensities of the first and second light sources, respectively, such that the predetermined diameter (dx) of the resultant light field on the operating site is maintained at a constant value when the distance between the lamp body and the operating site changes; and controlling the first and second light intensities of the first and second light sources, respectively, such that the predetermined diameter (dx) at which the preset relative central illuminance (Ecx) is generated is maintained at a substantially constant value as the distance between the lamp body and the operating site changes, wherein the first and second light sources are respectively assigned to first and second groups of light sources according to one or more criteria comprising diameters of light fields generated by light sources within the first and second groups of light sources and distances of the light sources within the first and second groups of light sources from the optical axis, wherein the control device is configured such that the light sources within the first and second groups of light sources can be controlled similarly and such that the first and second groups of light sources can be controlled independently of one another, and wherein the control device comprises a storage that stores a mapping, and wherein light intensities of the light sources in the first and second groups of light sources are stored as values associated with currents in the mapping, such that the values are retrievable by the control device in a mixing ratio that depends on the distance between the lamp body and the operating site.

15. The method according to claim 14, wherein the predetermined diameter (dx) is a factory preset value.

16. The method according to claim 14, wherein a central illuminance (Ec) of the resultant light field is a factory preset value.

17. The method according to claim 14, wherein an adjustment of the first and second light intensities to maintain the predetermined diameter (dx) at the substantially constant value is triggered following a change in the distance between the lamp body and the operating site.

18. The method according to claim 14, wherein the first light field has a relatively small diameter and the second light field has a relatively large diameter, wherein preventing an increase in the predetermined diameter (dx) of the resultant light field comprises one or both of increasing the first light intensity of the first light source and decreasing the second light intensity of the second light source, and wherein preventing a decrease in the predetermined diameter (dx) of the resultant light field comprises one or both of decreasing the first light intensity of the first light source and increasing the second light intensity of the second light source.

19. A surgical lamp for illuminating an operating site located along an optical axis, comprising:

a lamp body from which the optical axis extends, comprising a first light source and a second light source that respectively generate a first light field and a second light field having diameters that are substantially equal, wherein the operating site is located at a particular distance from the lamp body along the optical axis, wherein the first light field is associated with a first light distribution and the second light field is associated with a second light distribution that is substantially equal to the first light distribution, wherein the first light source has a fixed orientation with respect to a light-emitting surface of the lamp body, and the second light source has an adjustable orientation with respect to the light-emitting surface of the lamp body, and wherein the first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the optical axis;

a control device configured to control a first light intensity of the first light source, a second light intensity of the second light source, and a tilting angle of the second light source, such that the preset relative central illuminance (Ecx) is generated at the predetermined diameter (dx) at the particular distance; and a device for detecting a distance between the lamp body and the operating site along the optical axis, wherein the control device is configured to control the first and second light intensities of the first and second light sources, respectively, and the tilting angle of the second light source, such that the predetermined diameter (dx) of the resultant light field is maintained at a substantially constant value as the distance along the optical axis between the lamp body and the operating site changes.

20. The surgical lamp according to claim 19, wherein when the resultant light field is located at a maximum working distance, the predetermined diameter (dx) of the resultant light field is no greater than a minimum allowable predetermined diameter (dx).

21. The surgical lamp according to claim 19, wherein when the resultant light field is located at a distance greater than a maximum working distance, the predetermined diameter (dx) of the resultant light field is no greater than a minimum allowable predetermined diameter (dx).

22. The surgical lamp according to claim 19, further comprising a means for triggering one or both of adjustment of light intensities and adjustment of tilting angles of light sources of the lamp body.

23. The surgical lamp according to claim 22, wherein the means for triggering an adjustment of the light intensities or the tilting angle comprises a motion sensor, and the control device is configured to evaluate a detected distance between the lamp body and the operating site, such that the control device appropriately controls the first and second light sources following detection of a completed motion of the lamp body by the motion sensor.

24. The surgical lamp according to claim 19, wherein the control device is configured to ensure that a central illuminance (Ec) of the resultant light field conforms to the surgical lamp standard as the distance changes.

25. The surgical lamp according to claim 19, further comprising modules to which at least one of the first and second light sources are attached, wherein the first light source is attached to an inner module of the modules, and the second light source is attached to another module of the modules.

26. The surgical lamp according to claim 25, wherein a light-emitting surface of the lamp body or a light-emitting surface of the inner module is divided into an inner area (I) that has a substantially circular shape and at least one outer area (II) positioned adjacent the inner area (I), wherein the first light source is positioned along the inner area (I), and the second light source is positioned along the at least one outer area (II).

27. The surgical lamp according to claim 19, further comprising an input means connected to the control device for setting the predetermined diameter (dx) at which the preset relative central illuminance (Ecx) of the resultant light field is generated.

28. The surgical lamp according to claim 27, wherein the input means comprises a means for selecting among different preset predetermined diameters (dx) at which the preset relative central illuminance (Ecx) is generated.

29. The surgical lamp according to claim 19, wherein light sources of the lamp body are assigned to groups according to a tilting capability of the light sources, wherein the control device is configured such that the light sources within a group can be controlled similarly, and groups of light sources can be controlled independently of one another.

30. The surgical lamp according to claim 29, wherein the control device comprises a storage that stores a mapping, wherein tilting angles of the light sources are stored in the storage, and wherein light intensities of the light sources in the groups are stored as values associated with currents in the mapping, such that the tilting angles and the values are retrievable by the control device in a mixing ratio that depends on the distance between the lamp body and the operating site.

31. A method for operating a surgical lamp, comprising:
    detecting a change in a distance along an optical axis of the surgical lamp between a lamp body of the surgical lamp and an operating site,
    wherein the optical axis extends from the lamp body, and the lamp body comprises a first light source and a second light source that respectively generate a first light field and a second light field having diameters that are substantially equal, wherein the operating site is located at a particular distance from the lamp body along the optical axis,
    wherein the first light field is associated with a first light distribution and the second light field is associated with a second light distribution that is substantially equal to the first light distribution,
    wherein the first light source has a fixed orientation with respect to a light-emitting surface of the lamp body, and the second light source has an adjustable orientation with respect to the light-emitting surface of the lamp body,
    and wherein the first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the optical axis;
    a control device configured to control a first light intensity of the first light source, a second light intensity of the second light source, and a tilting angle of the second light source, such that the preset relative central illuminance (Ecx) is generated at the predetermined diameter (dx) at the particular distance; and
    a device for detecting a distance between the lamp body and the operating site along the optical axis,
    wherein the control device is configured to control the first and second light intensities of the first and second light sources, respectively, and the tilting angle of the second light source such that the predetermined diameter (dx) of the resultant light field is maintained at a substantially constant value as the distance between the lamp body and the operating site changes; and
    controlling the first and second light intensities of the first and second light sources, respectively, and the tilting angle of the second light source, such that the predetermined diameter (dx) at which the preset relative central illuminance (Ecx) is generated is maintained at a substantially constant value as the distance along the optical axis between the lamp body and the operating site changes.

32. The method according to claim 31, wherein the predetermined diameter (dx) is a factory preset value.

33. The method according to claim 31, wherein a central illuminance (Ec) of the resultant light field is a factory preset value.

34. The method according to claim 31, wherein one or both of an adjustment of the first and second light intensities and an adjustment of the tilting angle to maintain the predetermined diameter (dx) at a substantially constant value are triggered following a change in the distance between the lamp body and the operating site.

35. The method according to claim 34,
    wherein preventing an increase in the predetermined diameter (dx) of the resultant light field comprises tilting the second light source radially towards the optical axis and controlling the first and second light intensities of the first and second light sources, respectively, such that the predetermined diameter (dx) at which the relative central illuminance (Ecx) is generated is maintained at a substantially constant value, and
    wherein preventing a decrease in the predetermined diameter (dx) of the resultant light field comprises tilting the second light source radially away from the optical axis and controlling the first and second light intensities of the first and second light sources, respectively, such that the predetermined diameter (dx) at which the relative central illuminance (Ecx) is generated is maintained at a substantially constant value.

36. The method according to claim 35, wherein the control device is configured to ensure that a central illuminance (Ec) of the resultant light field conforms to the surgical lamp standard as the distance along the optical axis changes, and
    wherein preventing an increase in the predetermined diameter (dx) further comprises controlling the first and second light intensities of the first and second light sources, respectively, such that the central illuminance (Ec) of the resultant light field is maintained at a substantially constant value, and
    wherein preventing a decrease in the predetermined diameter (dx) further comprises controlling the first and second light intensities of the first and second light sources, respectively, such that the central illuminance (Ec) of the resultant light field is maintained at a substantially constant value.

37. The method according to claim 31, wherein when the resultant light field is located at a maximum allowable distance or at a distance greater than the maximum allowable distance, the predetermined diameter (dx) of the resultant light field is no greater than a minimum allowable predetermined diameter (dx).

38. A surgical lamp for illuminating an operating site located along a tiltable optical axis of the surgical lamp, comprising:
- a lamp body from which the tiltable optical axis extends, comprising a first light source and a second light source that respectively generate a first light field and a second light field having diameters that are substantially equal, wherein the operating site is located at a particular distance from the lamp body along the tiltable optical axis,
- wherein the first light field is associated with a first light distribution and the second light field is associated with a second light distribution that is substantially equal to the first light distribution,
- wherein the first and second light sources are tiltable with respect to a light-emitting surface of the lamp body, and wherein the first light source emits a light sheaf that defines the tiltable optical axis,
- and wherein the first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the tiltable optical axis;
- a control device configured to control a first light intensity of the first light source, a second light intensity of the second light source, and first and second tilting angles of the first and second light sources, respectively, such that the preset relative central illuminance (Ecx) is generated at the predetermined diameter (dx) at the particular distance; and
- a device for detecting a distance between the lamp body and the operating site along the tiltable optical axis,
- wherein the control device is configured to control the first and second light intensities and the first and second tilting angles of the first and second light sources, respectively, such that the predetermined diameter (dx) of the resultant light field is maintained at a substantially constant value as the distance along the tiltable optical axis between the lamp body and the operating site changes.

39. A surgical lamp for illuminating an operating site located along an optical axis, comprising:
- a lamp body from which the optical axis extends, comprising a first light source and a second light source that respectively generate a first light field and a second light field having diameters that are substantially equal, wherein the operating site is located at a particular distance from the lamp body along the optical axis,
- wherein the first light field is associated with a first light distribution and the second light field is associated with a second light distribution that is substantially equal to the first light distribution,
- wherein the first light source has a fixed orientation with respect to a light-emitting surface of the lamp body, and the second light source has an adjustable orientation with respect to the light-emitting surface of the lamp body,
- and wherein the first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the optical axis;
- a control device configured to control a tilting angle of the second light source such that the preset relative central illuminance (Ecx) is generated at the predetermined diameter (dx) at the particular distance; and
- a device for detecting a distance between the lamp body and the operating site along the optical axis,
- wherein the control device is configured to control the tilting angle of the second light source such that according to the tilting angle of the second light source, in combination with a first light intensity of the first light source and a second light intensity of the second light source, the predetermined diameter (dx) of the resultant light field is maintained at a substantially constant value as the distance along the optical axis between the lamp body and the operating site changes.

40. A surgical lamp for illuminating an operating site located along an optical axis of the surgical lamp, comprising:
- a lamp body from which the optical axis extends, comprising a first light source and a second light source that respectively generate a first light field and a second light field having diameters that are substantially equal, wherein the operating site is located at a particular distance from the lamp body along the optical axis,
- wherein the first light field is associated with a first light distribution and the second light field is associated with a second light distribution that is substantially equal to the first light distribution,
- wherein the first and second light sources respectively have a first adjustable orientation and a second adjustable orientation with respect to a light-emitting surface of the lamp body,
- and wherein the first and second light fields together produce a resultant light field that has a substantially circular shape and is associated with a resultant light distribution that conforms to a surgical lamp standard, such that a preset relative central illuminance (Ecx) of the light distribution is generated at a predetermined diameter (dx) of the resultant light field along the optical axis;
- a control device configured to control first and second tilting angles of the first and second light sources, respectively, such that the preset relative central illuminance (Ecx) is generated at the predetermined diameter (dx) at the particular distance; and
- a device for detecting a distance between the lamp body and the operating site along the optical axis,
- wherein the control device is configured to control the first and second tilting angles of the first and second light sources, respectively, such that according to the first and second tilting angles of the first and second light sources, in combination with a first light intensity of the first light source and a second light intensity of the second light source, the predetermined diameter (dx) of the resultant light field is maintained at a substantially constant value as the distance along the optical axis between the lamp body and the operating site changes.

* * * * *

UNITED STATES PATENT AND TRADEMARK OFFICE
CERTIFICATE OF CORRECTION

PATENT NO. : 9,119,668 B2  
APPLICATION NO. : 14/014740  
DATED : September 1, 2015  
INVENTOR(S) : Rudolf Marka et al.

It is certified that error appears in the above-identified patent and that said Letters Patent is hereby corrected as shown below:

On The Title Page, Item (56)

On page 2, column 2, at line 1 of "Other Publications" delete "Transmittal of Translation" and insert --Transmittal of Copies of Translation--.

In The Claims

Column 18, line 48, in Claim 10 delete "relative illuminance (Ecx)" and insert --relative central illuminance (Ecx)--.

Column 18, lines 52-53, in Claim 11 delete "relative illuminance (Ecx)" and insert --relative central illuminance (Ecx)--.

Signed and Sealed this  
Sixteenth Day of February, 2016

Michelle K. Lee  
*Director of the United States Patent and Trademark Office*